(12) United States Patent
Pandey et al.

(10) Patent No.: US 7,329,655 B2
(45) Date of Patent: Feb. 12, 2008

(54) NITROGENOUS HETEROCYCLIC COMPOUNDS

(75) Inventors: Anjali Pandey, Fremont, CA (US); Robert M. Scarborough, Half Moon Bay, CA (US); Kenji Matsuno, Tokyo (JP); Michio Ichimura, Tokyo (JP); Yuji Nomoto, Shizuoka (JP); Shinichi Ide, Tokyo (JP); Eiji Tsukuda, Tokyo (JP); Junko Sasaki, Akita (JP); Shoji Oda, Tokyo (JP)

(73) Assignees: Millennium Pharmaceuticals, Inc., Cambridge, MA (US); Kyowa Hakko Kogyo Co., Ltd., Tokyo (JP)

( * ) Notice: Subject to any disclaimer, the term of this patent is extended or adjusted under 35 U.S.C. 154(b) by 511 days.

(21) Appl. No.: 10/344,625

(22) PCT Filed: Aug. 17, 2001

(86) PCT No.: PCT/US01/41750

§ 371 (c)(1),
(2), (4) Date: Mar. 18, 2004

(87) PCT Pub. No.: WO02/16361

PCT Pub. Date: Feb. 28, 2002

(65) Prior Publication Data

US 2004/0176594 A1    Sep. 9, 2004

Related U.S. Application Data

(60) Provisional application No. 60/226,121, filed on Aug. 18, 2000.

(51) Int. Cl.
*A61K 31/54* (2006.01)
*C07D 417/14* (2006.01)
*C07D 413/14* (2006.01)
*C07D 43/14* (2006.01)

(52) U.S. Cl. .............. 514/227.5; 514/231.2; 544/60; 544/116; 544/284

(58) Field of Classification Search .......... 544/60, 544/284, 116; 514/227.5, 231.2
See application file for complete search history.

(56) References Cited

U.S. PATENT DOCUMENTS 6,169,088 B1 * 1/2001 Matsuno et al. ....... 514/252.16
6,207,667 B1    3/2001 Matsuno et al.
6,750,218 B2 * 6/2004 Matsuno et al. .......... 514/248
6,960,580 B2 * 11/2005 Scarborough et al. ... 514/228.2
2002/0068734 A1    6/2002 Matsuno et al.

FOREIGN PATENT DOCUMENTS

| EP | 0 882 717 A | 12/1998 |
| EP | 1 067 123 A | 1/2001 |
| WO | WO 02/16351 A2 | 2/2002 |
| WO | WO 02/16360 A2 | 2/2002 |
| WO | WO 02/16362 A2 | 2/2002 |
| WO | WO 02/072578 A2 | 9/2002 |

OTHER PUBLICATIONS

Agrawal, Vijai et al.: "Antiparasitic agents. Part VI: Synthesis of 7-chloro-4-(4-substituted-phenylanino)- and 7-chloro-4-(4-substituted-piperazin-1-yl)quinolines as potential antiparasitic agents" Indian J. Chem., Sect. B (1987), 26(B)6, pp. 550-555.

Heath, Julie, et al. "Identification of 4-piperazin-1-yl-quinazoline template based aryl and benzyl thioureas as potent, selective, and orally bioavailable inhibitors of platelet-derived growth factor (PDGF) receptor." Bioorganic & Medicinal Chemistry Letters 14 (2004) pp. 4867-4872.

Matsuno, Kenji, et al. "Potent and Selective Inhibitors of Platelet-Derived Growth Factor Receptor Phosphorylation. Part 4: Structure-Activity Relationships for Substituents on the Quinazoline Moiety of 4-[4-(*N*-Substituted(thio)carbamoyl)-1-piperaziny]-6,7-dimethoxyquinazoline Derivatives." Bioorganic Medicinal Chemistry Letters 13 (2003) pp. 3001-3004.

Matsuno, Kenji, et al. "Potent and Selective Inhibitors of Platelet-Derived Growth Factor Receptor Phosphorylation. 3. Replacement of Quinazoline Moiety and Improvement of Metabolic Polymorphism of 4-[4-(*N*-Substituted (thio) carbamoyl)-1-piperazinyl]-6.7-dimethoxyquinazoline Derivatives." J.Med. Chem. (2003) 46, pp. 4910-4925.

* cited by examiner

*Primary Examiner*—Kamal A. Saeed
(74) *Attorney, Agent, or Firm*—Townsend and Townsend and Crew LLP

(57) ABSTRACT

The present invention relates to nitrogen-containing heterocyclic compounds and pharmaceutically acceptable salts thereof which have inhibitory activity on the phosphorylation of kinases, which inhibits the activity of such kinases. The invention is also related to a method of inhibiting kinases and treating disease states in a mammal by inhibiting the phosphorylation of kinases. In a particular aspect the present invention provides nitrogen-containing heterocyclic compounds and pharmaceutically acceptable salts thereof which inhibit phosphorylation of a PDGF receptor to hinder abnormal cell growth and cell wandering, and a method for preventing or treating cell-proliferative diseases such as arteriosclerosis, vascular reobstruction, cancer and glomerulosclerosis.

8 Claims, No Drawings

NITROGENOUS HETEROCYCLIC COMPOUNDS

This application is a 371 of PCT/US01/41750 filed Aug. 17, 2001 which claims benefit of U.S. Provisional Application Ser. No. 60/226,121 filed Aug. 18, 2000, the contents of which are incorporated herein.

TECHNICAL FIELD

The present invention relates to nitrogen-containing heterocyclic compounds and pharmaceutically acceptable salts thereof which have inhibitory activity on the phosphorylation of kinases, which inhibits the activity of such kinases. The invention is also related to a method of inhibiting kinases and treating disease states in a mammal by inhibiting the phosphorylation of kinases.

BACKGROUND ART

PDGF (platelet-derived growth factor) is known to act as an aggravating factor for cell-proliferative diseases such as arteriosclerosis, vascular reobstruction after percutaneous coronary angioplasty and bypass operation, cancer, glomerulonephritis, glomerulosclerosis, psoriasis and articular rheumatism [Cell, 46, 155-169 (1986); Science, 253, 1129-1132 (1991); Nippon Rinsho (Japanese J. of Clinical Medicine), 50, 3038-3045. (1992); Nephrol Dial Transplant, 10, 787-795 (1995); Kidney International, 43 (Suppl. 39), 86-89 (1993); Journal of Rheumatology, 21, 1507-1511 (1994); Scandinavian Journal of Immunology, 27, 285-294 (1988), etc.].

As for quinazoline derivatives which are useful as drugs, N,N-dimethyl-4-(6,7-dimethoxy-4-quinazolinyl)-1-piperazine carboxamide is described as a bronchodilator in South African Patent No. 67 06512 (1968). Dinlethoxyquinazoline derivatives are described as inhibitors of phosphorylation of epidermal growth factor (EGF) receptor in Japanese Published Unexamined Patent Application No. 208911/93 and WO 96/09294. Quinoline derivatives having benzodiazepin receptor agonist activity are described in Pharmacology Biochemistry and Behavior, 53, 87-97 (1996) and European Journal of Medicinal Chemistry, 31, 417-425 (1996), and quinoline derivatives which are useful as anti-parasite agents are described in Indian Journal of Chemistry, 26B, 550-555 (1987).

Inhibitors of phosphorylation of PDGF receptor so far known include bismono- and bicyclic aryl compounds and heteroaryl compounds (WO 92/20642), quinoxaline derivatives [Cancer Research, 54, 6106 (1994)], pyrimidine derivatives (Japanese Published Unexamined Patent Application No. 87834/94) and dimethoxyquinoline derivatives [Abstracts of the 16th Annual Meeting of the Pharmaceutical Society of Japan (Kanazawa) (1996), 2, p. 275, 29(C2) 15-2].

DISCLOSURE OF THE INVENTION

An object of the present invention is to provide nitrogen-containing heterocyclic compounds and pharmaceutically acceptable salts thereof which have inhibitory activity on the phosphorylation of kinases, which inhibits the activity of the kinases. Particularly, important kinase inhibition according to the invention is of receptor tyrosine kinases including platelet-derived growth factor (PDGF) receptor, Flt3, CSF-1R, epidermal growth factor receptor (EGRF), fibroblast growth factor (FGF), vascular endothelial growth factor receptor (VEGFR) and others. Another class of kinase inhibition according to the invention is inhibitory activity nonreceptor tyrosine kinases including src and abl, and the like. A third class of kinase inhibition according to the invention is inhibitory activity toward serine/threonine kinases, including such kinases as MAPK, MEK and cyclin dependent kinases (CDKs) that mediate cell prolifetation, AKT and CDK such that mediate cell survival and NIK that regulate inflammatory responses. Inhibition of such kinases can be used to treat diseases involving cell survival, proliferation and migration, including cardiovascular disease, such as arteriosclerosis and vascular reobstruction, cancer, glomerulosclerosis fibrotic diseases and inflammation, as well as the general treatment of cell-proliferative diseases.

In a preferred embodiment, the present invention provides compounds and pharmaceutically acceptable salts thereof which inhibit or prevent inhibition of phosphorylation of at least one PDGF receptor by at least one tyrosine kinase. Such PDGF receptor kinase inhibition can hinder abnormal cell growth and cell wandering, and thus such compounds are useful for the prevention or treatment of cell-proliferative diseases such as arteriosclerosis, vascular reobstruction, cancer and glomerulosclerosis.

The present invention relates to piperazine thiourea compounds. Preferred such compounds are nitrogen-containing heterocyclic compounds represented by formula I as follows:

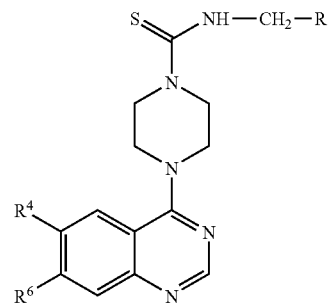

wherein
R is a member selected from the group consisting of:
(a) phenyl, which is independently substituted with 0-2 $R^1$ substituents;
(b) naphthyl, which is independently substituted with 0-2 $R^1$ substituents; and
(c) a monocyclic or fused bicyclic heterocyclic ring system having from 5 to 10 ring atoms, wherein 1-4 ring atoms of the ring system are selected from the group consisting of N, O and S, and wherein the ring system may be substituted with 0-2 $R^1$ substituents; and (d)

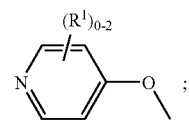

$R^1$ is a member selected from the group consisting of:
halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —NO$_2$, —(CH$_2$)$_m$NR$^2$R$^3$, SO$_2$NR$^2$R$^3$, SO$_2$R$^2$, CF$_3$, OR$^2$, and a 5-6 membered aromatic heterocyclic system containing from 1-4 heteroatoms selected from N, O and S, wherein from 1-4 hydrogen atoms on the aromatic heterocyclic system may be independently replaced with a member selected from the group consisting of halo, —$C_1$-$C_4$-alkyl, —CN, —$C_{1-4}$alkyl, —$C_{2-6}$alkenyl, —$C_{2-6}$alkynyl, —$C_{3-8}$cycloalkyl, —$C_{0-4}$alkyl $C_{3-8}$cycloalkyl and —$NO_2$;

$R^2$ and $R^3$ are independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl, $C_{0-4}$alkylnaphthyl, $C_{0-4}$alkylindolyl, and $C_{0-4}$alkylisoquinolyl, wherein from 1-4 hydrogen atoms on the ring atoms of the phenyl, naphthyl, indolyl, and isoquinolyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

m is an integer of 0-2;

$R^4$ and $R^6$ are each independently a member selected from the group consisting of:

H, —O—$CH_3$, —O(—$CH_2$)—$CH_3$, —O—$CH_2$—CH=$CH_2$, —O—$CH_2$—C4CH and —O(—$CH_2$)$_n$—$R^5$;

n is 2 or 3;

$R^5$ is a member selected from the group consisting of:

—OH, —O—$CH_3$, —O—$CH_2$—$CH_3$, —$NH_2$, —N(—$CH_3$)$_2$, —NH(—$CH_2$-phenyl), —NH(-Phenyl), —CN

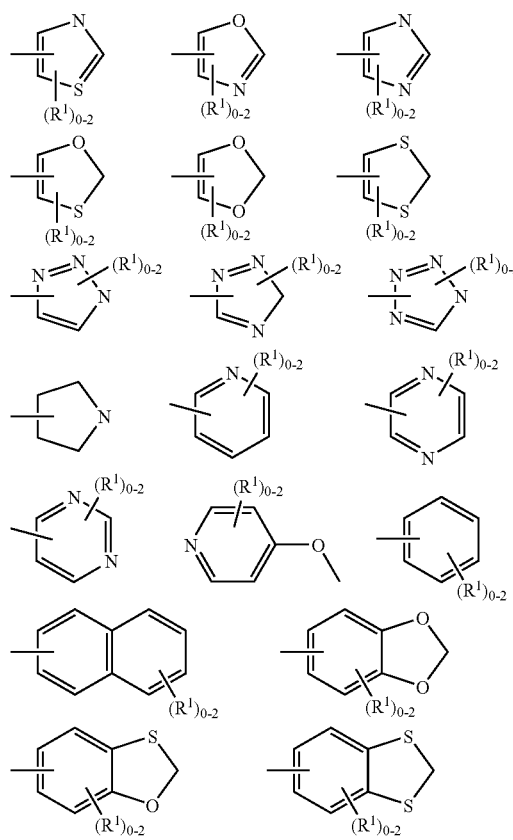

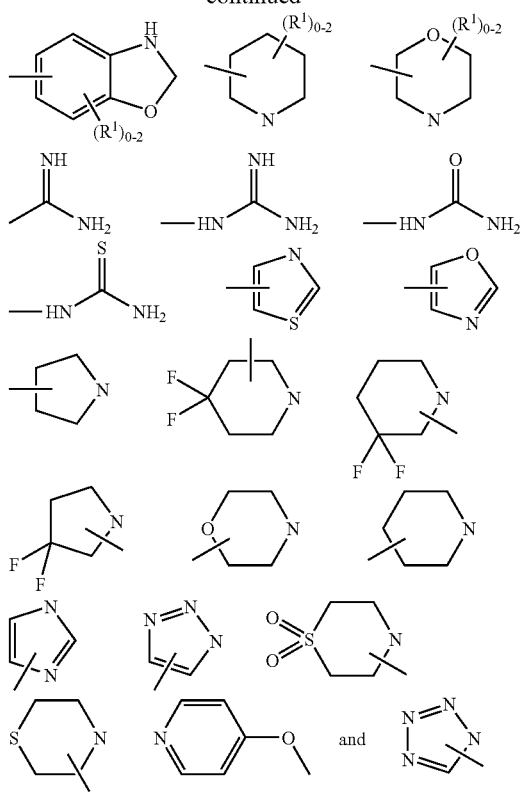

and all pharmaceutically acceptable isomers, salts, hydrates, solvates and prodrug derivatives thereof.

The pharmaceutically acceptable salts of the compounds according to formula (I) include pharmaceutically acceptable acid addition salts, metal salts, ammonium salts, organic amine addition salts, amino acid addition salts, etc. Examples of the pharmaceutically acceptable acid addition salts of the compounds of formula (I) are inorganic acid addition salts such as hydrochloride, sulfate and phosphate, and organic acid addition salts such as acetate, maleate, fumarate, tartrate, citrate and methanesulfonate. Examples of the pharmaceutically acceptable metal salts are alkali metal salts such as sodium salt and potassium salt, alkaline earth metal salts such as magnesium salt and calcium salt, aluminum salt and zinc salt. Examples of the pharmaceutically acceptable ammonium salts are ammonium salt and tetramethyl ammonium salt. Examples of the pharmaceutically acceptable organic amine addition salts include heterocyclic amine salts such as morpholine and piperidine salts. Examples of the pharmaceutically acceptable amino acid addition salts are salts with lysine, glycine and phenylalanine.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified, alkenyl and alkinyl each refer to radicals having from 2-12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

As used herein, the terms "carbocyclic ring structure" and "$C_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0] bicyclononane, [4.4.0]bicyclodecane (decalin), 2.2.2]bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5-7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement(s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocylic and bicyclic heterocylic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzo furanyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocylic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to —CH$_2$—. The term "Bu" refers to "butyl" or —CH$_2$CH$_2$CH$_2$CH$_2$—; the term "Ph" refers to "phenyl"; the term "Me" refers to "methyl" or —CH$_3$; the term "Et" refers to "ethyl" or —H$_2$CH$_3$; the term "Bu(t)" or "t-Bu" refer to "tert-butyl" or —C(CH$_3$)$_4$.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by iii vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

Preferred Embodiments

In one preferred embodiment the present invention relates to nitrogen-containing heterocyclic thiourea compounds represented by formula I as follows:

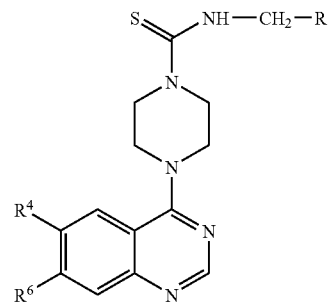

wherein

R is a member selected from the group consisting of:
(a) phenyl, which is independently substituted with 0-2 R$^1$ substituents;
(b) naphthyl, which is independently substituted with 0-2 R$^1$ substituents;
(c) a monocyclic or fused bicyclic heterocyclic ring system having from 5 to 10 ring atoms, wherein 1-4 ring atoms of the ring system are selected from the group consisting of N, O and S, and wherein the ring system may be substituted with 0-2 R$^1$ substituents; and (d)

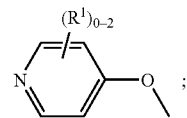

R¹ is a member selected from the group consisting of:
- halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —NO₂, —(CH₂)$_m$NR²R³, SO₂NR²R³, SO₂R², CF₃, OR², and a 5-6 membered aromatic heterocyclic system containing from 1-4 heteroatoms selected from N, O and S, wherein from 1-4 hydrogen atoms on the aromatic heterocyclic system may be independently replaced with a member selected from the group consisting of halo, —C₁-C₄-alkyl, —CN, —$C_{1-4}$alkyl, —$C_{2-6}$alkenyl, —$C_{2-6}$alkynyl, —$C_{3-8}$cycloalkyl, —$C_{0-4}$alkyl $C_{3-8}$cycloalkyl and —NO₂;

R² and R³ are independently selected from the group consisting of:
- H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl, $C_{0-4}$alkylnaphthyl, $C_{0-4}$alkylindolyl, and $C_{0-4}$alkylisoquinolyl, wherein from 1-4 hydrogen atoms on the ring atoms of the phenyl, naphthyl, indolyl, or isoquinolyl moieties may be independently replaced with a member selected from the group consisting of halo, $C_{1-4}$alkyl, $C_{2-6}$alkenyl, $C_{2-6}$alkynyl, $C_{3-8}$cycloalkyl, $CO_4$alkyl$C_{3-8}$cycloalkyl, —CN, and —NO₂;

m is an integer of 0-2;

R⁴ and R⁶ are each independently a member selected from the group consisting of:
- —O—CH₃, —O(—CH₂)—CH₃, —O—CH₂—CH=CH₂, —O—CH₂—C4CH and —O(—CH₂)$_n$—R⁵;

n is 2 or 3;

R⁵ is a member selected from the group consisting of:
- —OH, —O—CH₃, —O—CH₂—CH₃, —NH₂, —N(—CH₃)₂, —NH(—CH₂-phenyl), —NH(-phenyl), —CN

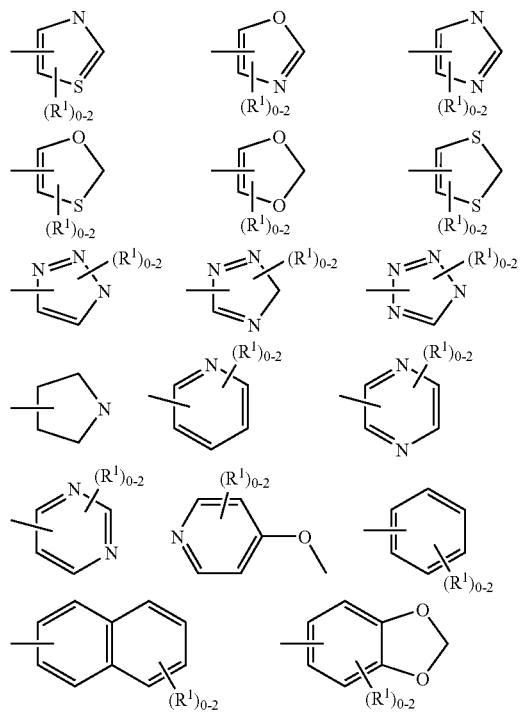

and all pharmaceutically acceptable isomers, salts, hydrates, solvates and prodrug derivatives thereof.

Particularly preferred compounds according to formula above are such compounds wherein R¹ is a member selected from the group consisting of CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy, and position isomers and homologs thereof, and all pharmaceutically acceptable isomers, salts, hydrates, solvates and prodrug derivatives of such compounds.

Also, particularly preferred are such compounds wherein R⁶ and R⁴ are different and one of R⁶ and R⁴ is —O—CH₃, and all pharmaceutically acceptable isomers salts, hydrates, solvates and prodrug derivatives of such compounds.

The pharmaceutically acceptable salts of the compounds according to formula (I) include pharmaceutically acceptable acid addition salts, metal salts, ammonium salts, organic amine addition salts, amino acid addition salts, etc. Examples of the pharmaceutically acceptable acid addition salts of the compounds of formula (I) are inorganic acid addition salts such as hydrochloride, sulfate and phosphate, and organic acid addition salts such as acetate, maleate, fumarate, tartrate, citrate and methanesulfonate. Examples of the pharmaceutically acceptable metal salts are alkali metal salts such as sodium salt and potassium salt, alkaline earth metal salts such as magnesium salt and calcium salt, aluminum salt and zinc salt. Examples of the pharmaceutically acceptable ammonium salts are ammonium salt and tetramethyl ammonium salt. Examples of the pharmaceutically acceptable organic amine addition salts include heterocyclic amine salts such as morpholine and piperidine salts. Examples of the pharmaceutically acceptable amino acid addition salts are salts with lysine, glycine and phenylalanine.

In a preferred embodiment the invention provides compounds according to formula I(a) and formula I(b) as follows:

Formula I(a)

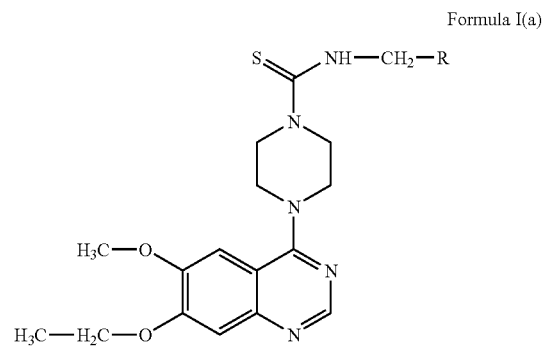

-continued

Formula I(b)

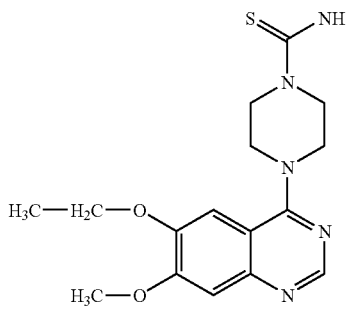

wherein
R is defined as described above for formula I
and all pharmaceutically acceptable isomers, salts, hydrates, solvates and prodrug derivatives thereof.

In another preferred embodiment the invention provides compounds according to formula (Ic) and formula (Id) as follows:

Formula I(c)

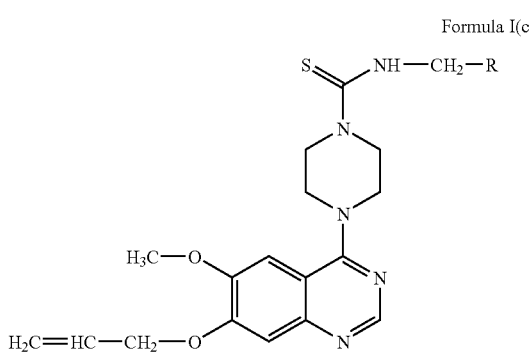

Formula I(d)

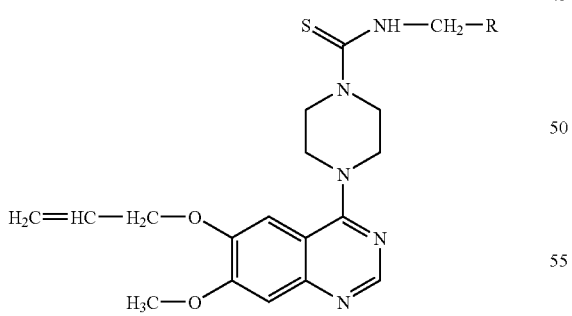

wherein
R is defined as described above for formula I
and all pharmaceutically acceptable isomers, salts, hydrates, solvates and prodrug derivatives thereof.

In still another preferred embodiment the invention provides compounds according to formula I(e) and formula I(f) as follows:

Formula I(e)

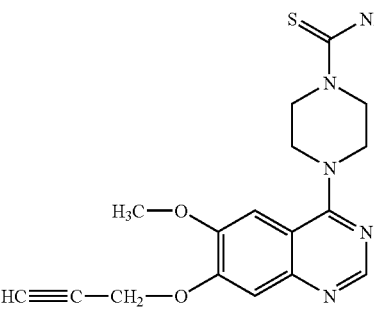

Formula I(f)

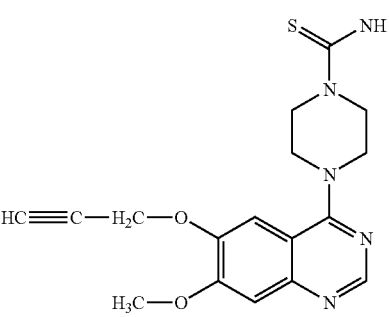

wherein
R is defined as described above for formula I
and all pharmaceutically acceptable isomers, salts, hydrates, solvates and prodrug derivatives thereof.

In yet another preferred embodiment the invention provides compounds according to formula I(g) and formula I(h) as follows:

Formula I(g)

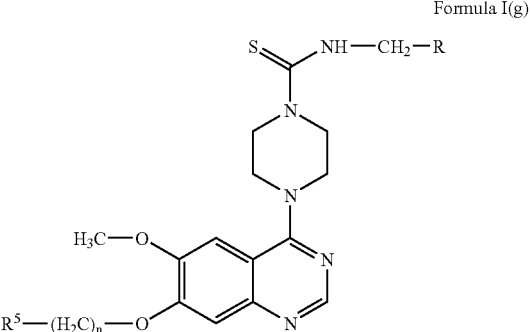

Formula I(h)

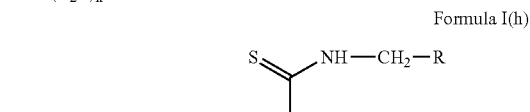
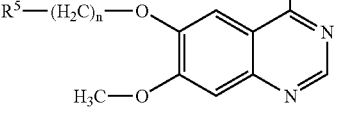

wherein
R and n are defined as described above for formula I;
$R^5$ is a member selected from the group consisting of:
—OH, —O—CH$_3$, —O—CH$_2$—CH$_3$, —NH$_2$, —N(—CH$_3$)$_2$, —NH(—CH$_2$-phenyl), —NH(-phenyl), —CN

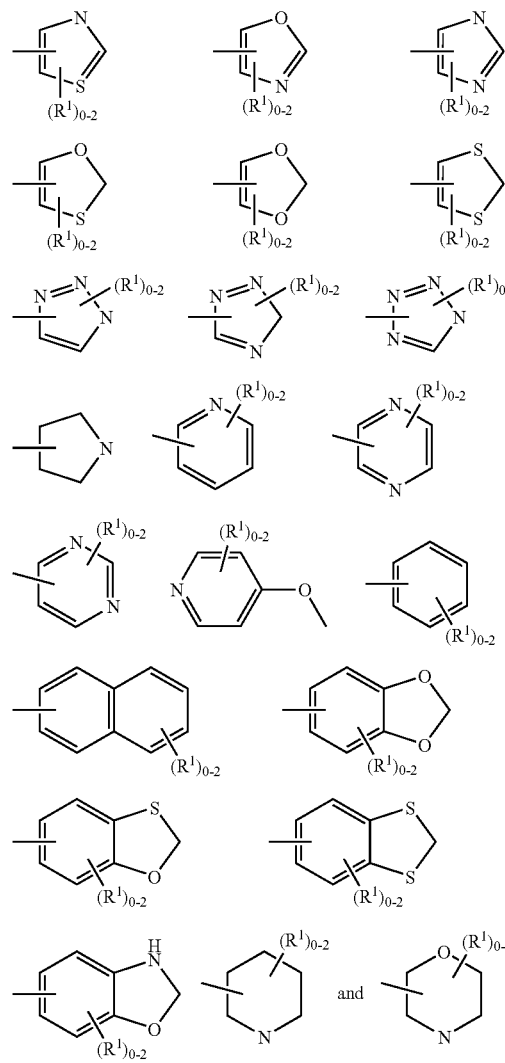

and all pharmaceutically acceptable isomers, salts, hydrates, solvates and prodrug derivatives thereof A even further preferred embodiment of the invention is a group of compounds according to each of formula I(a)-I(h), wherein R is a member selected from the group consisting of:

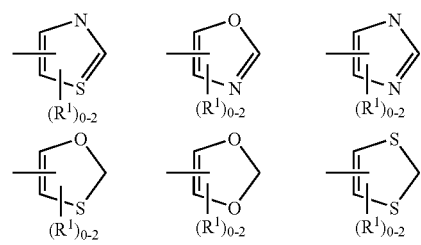

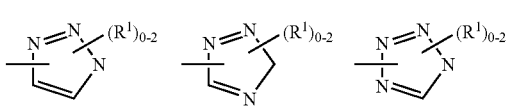
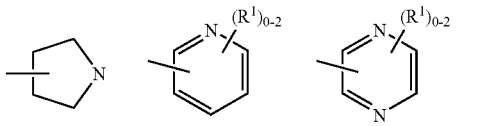
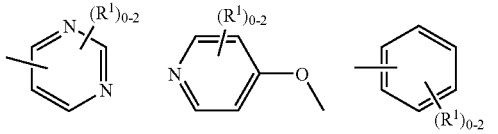
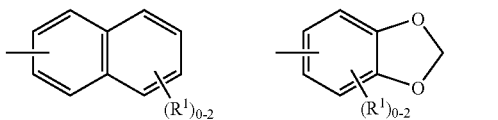
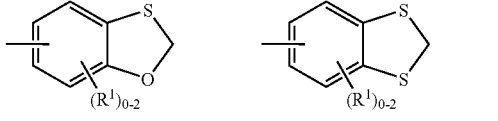
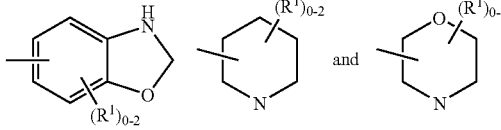

and all pharmaceutically acceptable isomers, salts, hydrates, solvates and prodrug, derivatives thereof.

Another preferred embodiment of the invention is a group of compounds of formula I according to formula II, as follows:

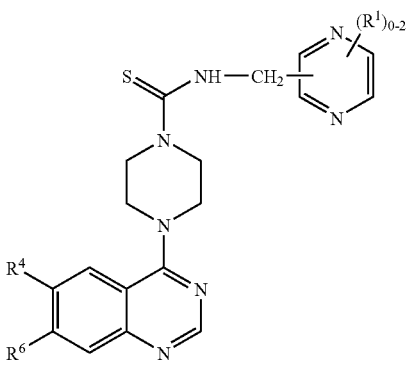

wherein $R^1$, $R^4$ and $R^6$ are defined as above for formula I, and all pharmaceutically acceptable isomers, salts, hydrates, solvates and prodrug derivatives thereof.

More preferred such compounds of formula II are compounds of the formula IIa as follows:

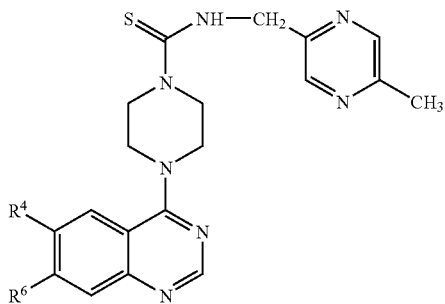

wherein $R^4$ and $R^6$ are defined as above for formula I, and all pharmaceutically acceptable isomers, salts, hydrates, solvates and prodrug derivatives thereof.

Another preferred embodiment of the invention is a group of compounds of formula I according to formula III, as follows:

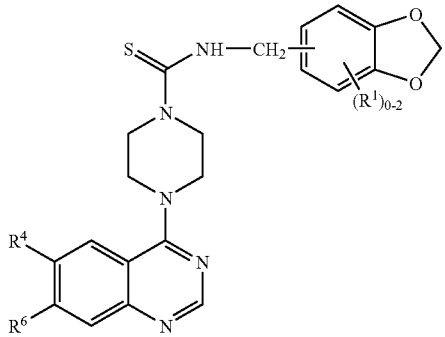

wherein $R^1$, $R^4$ and $R^6$ are defined as above for formula I, and all pharmaceutically acceptable isomers, salts, hydrates, solvates and prodrug derivatives thereof.

A preferred embodiment of the invention is a group of compounds according to each of formula I(a)-I(h), wherein R is a member selected from the group consisting of:

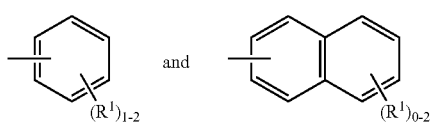

and all pharmaceutically acceptable isomers, salts, hydrates, solvates and prodrug derivatives thereof.

Another preferred embodiment of the invention is a group of compounds of formula I according to formula II, as follows:

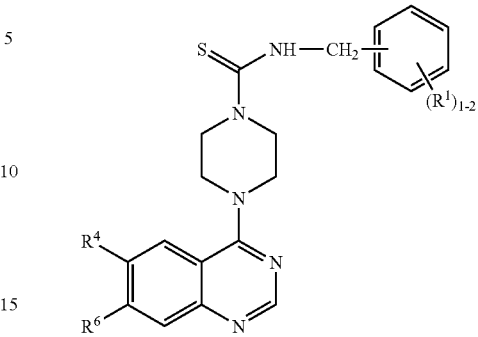

wherein $R^1$, $R^4$ and $R^6$ are defined as above for formula I, and all pharmaceutically acceptable isomers, salts, hydrates, solvates and prodrug derivatives thereof.

Another preferred embodiment of the invention is a group of compounds of formula I according to formula III, as follows:

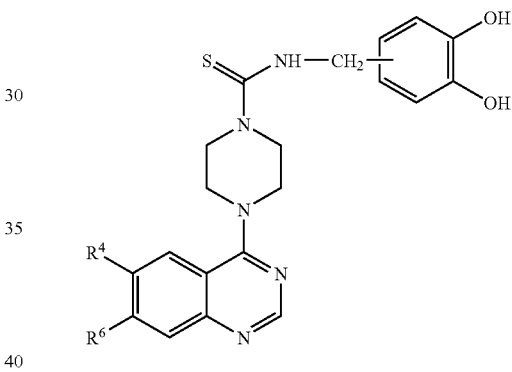

wherein $R^4$ and $R^6$ are defined as above for formula I, and all pharmaceutically acceptable isomers, salts, hydrates, solvates and prodrug derivatives thereof.

Also preferred are compounds of formula I having the formula IV as follows:

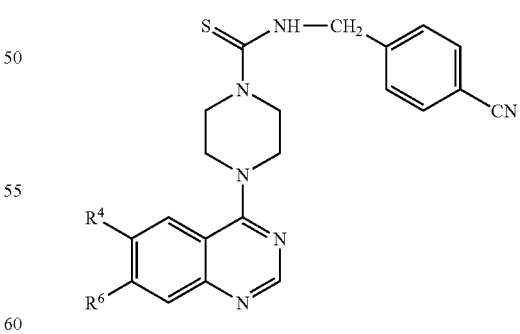

wherein $R^4$ and $R^6$ are defined as above for formula I, and all pharmaceutically acceptable isomers, salts, hydrates, solvates and prodrug derivatives thereof.

Another preferred embodiment of the invention is a group of compounds of formula I according to formula V, as follows:

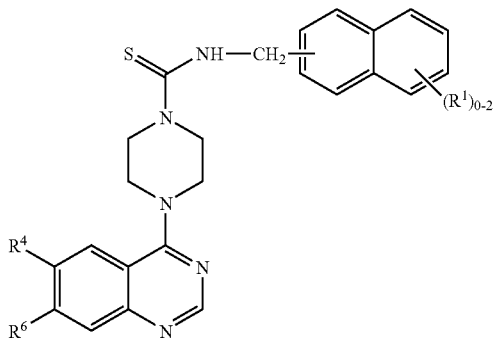

wherein $R^1$, $R^4$ and $R^6$ are defined as above for formula I, and all pharmaceutically acceptable isomers, salts, hydrates, solvates and prodrug derivatives thereof.

Another preferred embodiment of the invention is a group of compounds of formula I, having the following formulae:

[(2H-benzo[d]1,3-dioxolan-5-ylmethyl)amino]{4-[6-methoxy-7-(2-piperidylethoxy)quinazolin-4-yl]piperazinyl}methane-1-thione

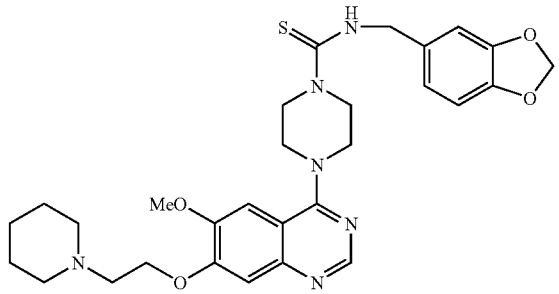

[(2H-benzo[d]1,3-dioxolan-5-ylmethyl)amino]{4-[6-methoxy-7-(2-morpholin-4-ylethoxy)quinazolin-4-yl]piperazinyl}methane-1-thione

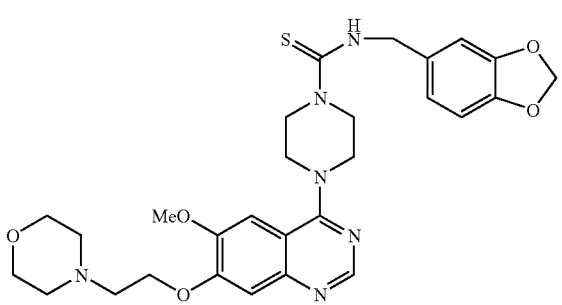

{4-[6-methoxy-7-(2-morpholin-4-ylethoxy)quinazolin-4-yl]piperazinyl}{[(5-methylpyrazin-2-yl)methyl]amino}methane-1-thione

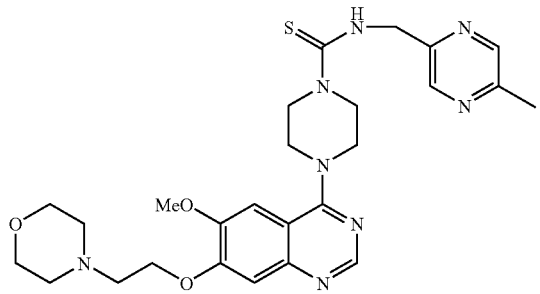

{4-[6-methoxy-7-(2-piperidylethoxy)quinazolin-4-yl]piperazinyl}{[(5-methylpyrazin-2-yl)methyl]amino}methane-1-thione

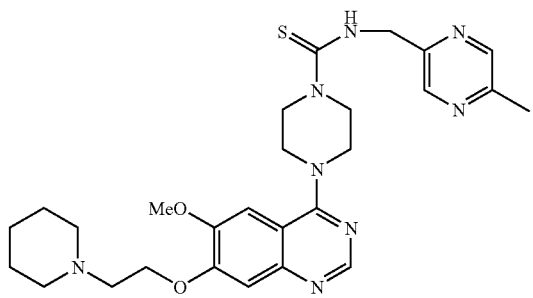

4-{[({4-[6-methoxy-7-(2-piperidylethoxy)quinazolin-4-yl]piperazinyl}thioxomethyl)amino]methyl}benzenecarbonitrile

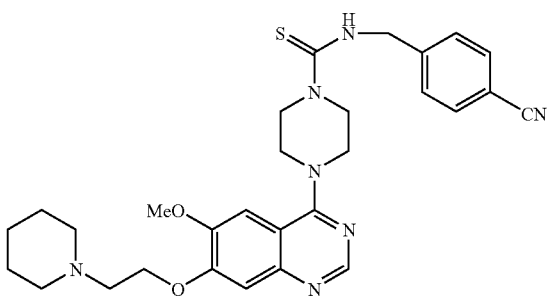

| 19 | 20 |
|---|---|
| {[(4-bromophenyl)methyl]amino)}{4-[6-methoxy-7-(2-piperidylethoxy)quinazolin-4-yl]piperazinyl}methane-1-thione | [(2-furylmethyl)amino]{4-[6-methoxy-7-(2-piperidylethoxy)quinazolin-4-yl]piperazinyl}methane-1-thione |

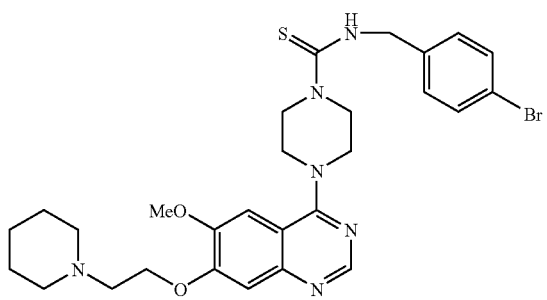

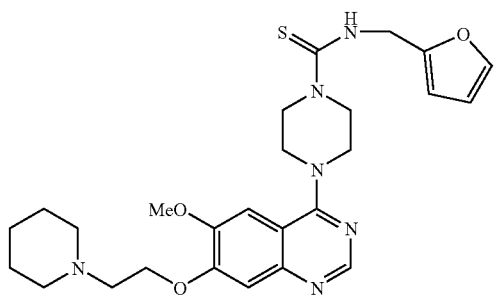

{4-[6-methoxy-7-(2-piperidylethoxy)quinazolin-4-yl]piperazinyl}[pyrazin-2-ylmethyl)amino]methane-1-thione {4-[6-methoxy-7-(2-piperidylethoxy)quinazolin-4-yl]piperazinyl}[(2-thienylmethyl) amino]methane-1-thione

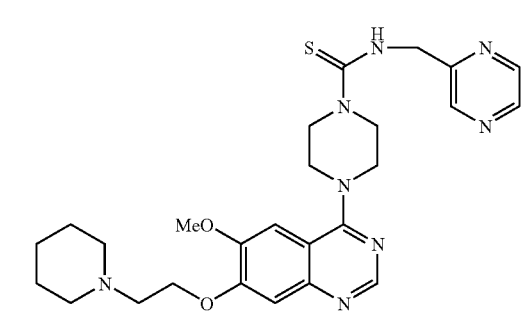

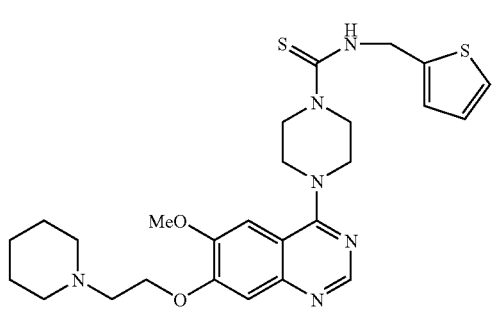

{4-[6-methoxy-7-(2-piperidylethoxy)quinazolin-4-yl]piperazinyl}[(3-pyridyl methyl)amino]methane-1-thione {4-[6-methoxy-7-(2-piperidylethoxy)quinazolin-4-yl]piperazinyl}[(1,3-thiazol-2-ylmethyl)amino]methane-1-thione

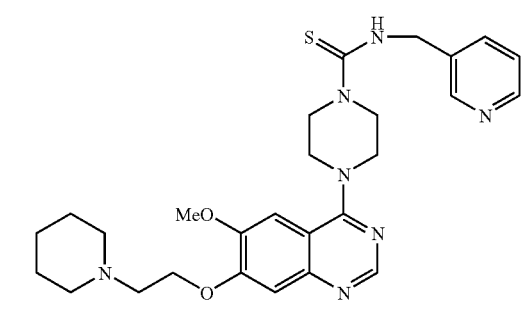

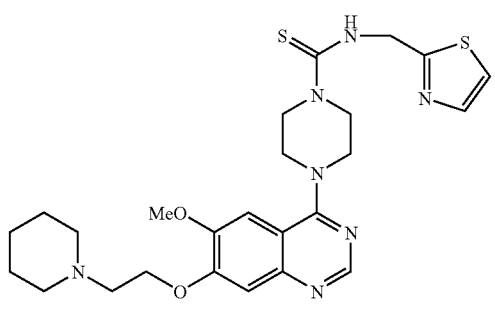

| 21 | 22 |
|---|---|

[(imidazol-2-ylmethyl)amino]{4-[6-methoxy-7-(2-piperidylethoxy)quinazolin-4-yl]piperazinyl}methane-1-thione {4-[6-methoxy-7-(3-piperidylpropoxy)quinazolin-4-yl]piperazinyl}[(3-pyridylmethyl)amino]methane-1-thione

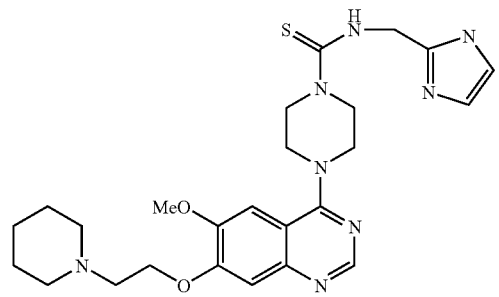

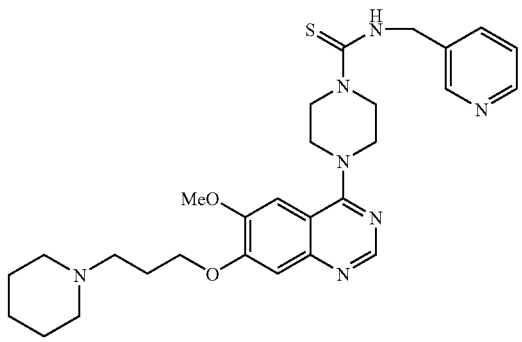

{4-[6-methoxy-7-(3-piperidylpropoxy)quinazolin-4-yl]piperazinyl}{[(5-methylpyrazin-2-yl)methyl]amino}methane-1-thione {4-[6-methoxy-7-(3-morpholin-4-ylpropoxy)quinazolin-4-yl]piperazinyl}[(3-pyridylmethyl)amino]methane-1-thione

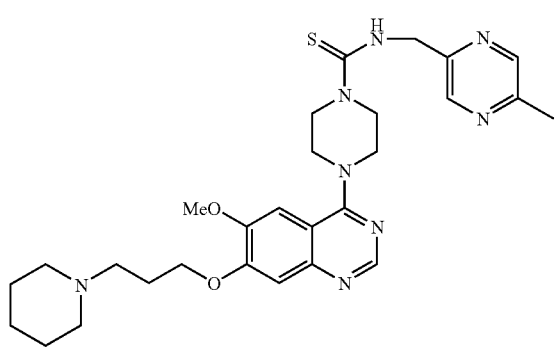

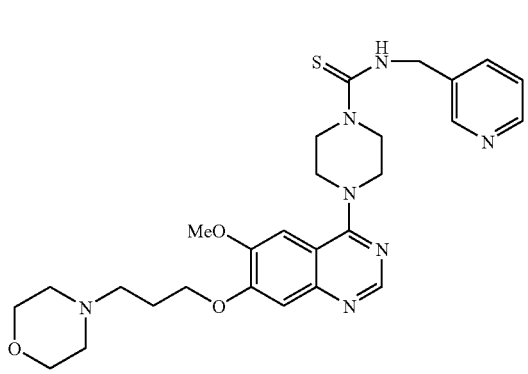

{4-[6-methoxy-7-(3-morpholin-4-ylpropoxy)quinazolin-4-yl]piperazinyl}{[(5-methylpyrazin-2-yl)methyl]amino}methane-1-thione {4-[6-methoxy-7-(3-piperidylpropoxy)quinazolin-4-yl]piperazinyl}[(1,3-thiazol-2-ylmethyl)amino]methane-1-thione

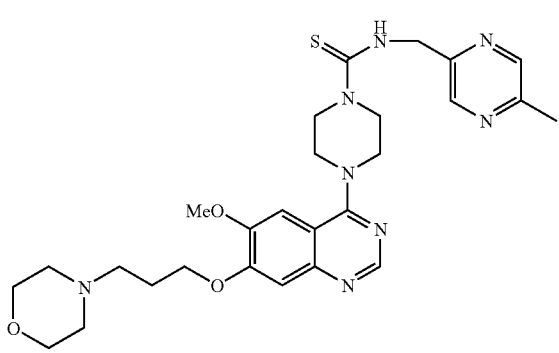

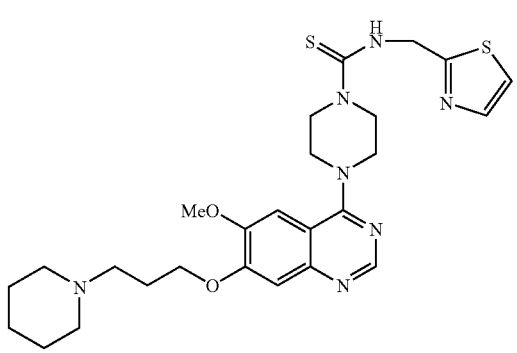

23
{4-[6-methoxy-7-(3-morpholin-4-ylpropoxy)quinazolin-4-yl]piperazinyl}[(1,3-thiazol-2-ylmethyl)amino]methane-1-thione

24
{4-[6-methoxy-7-(3-piperidylpropoxy)quinazolin-4-yl]piperazinyl}{[(6-phenyl(3-pyridyl))methyl]amino}methane-1-thione

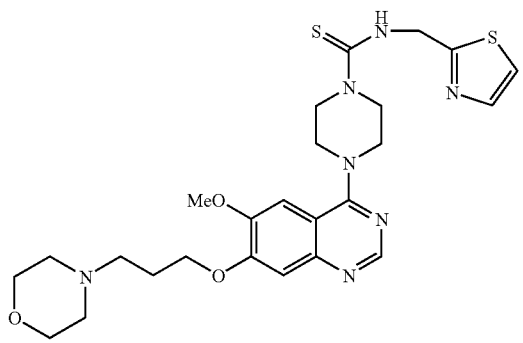

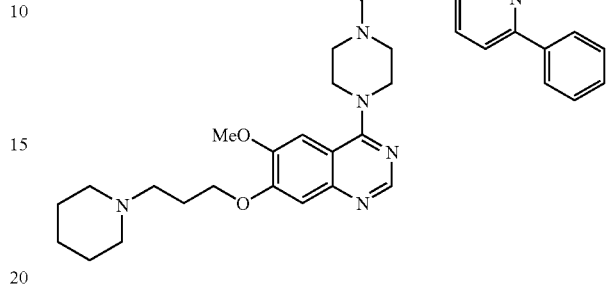

[(imidazol-2-ylmethyl)amino]{4-[6-methoxy-7-(3-morpholin-4-ylpropoxy)quinazolin-4-yl]piperazinyl}methane-1-thione {4-[6-methoxy-7-(3-piperidylpropoxy)quinazolin-4-yl]piperazinyl}{[(6-methyl(3-pyridyl))methyl]amino}methane-1-thione

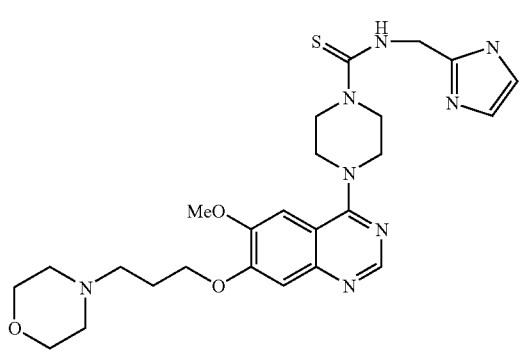

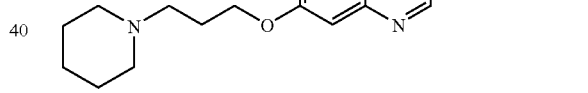

[(imidazol-2-ylmethyl)amino]{4-[6-methoxy-7-(3-piperidylpropoxy)quinazolin-4-yl]piperazinyl}methane-1-thione {4-[6-methoxy-7-(3-piperidylpropoxy)quinazolin-4-yl]piperazinyl}({[6-(trifluoromethyl)(3-pyridyl)]methyl}amino)methane-1-thione

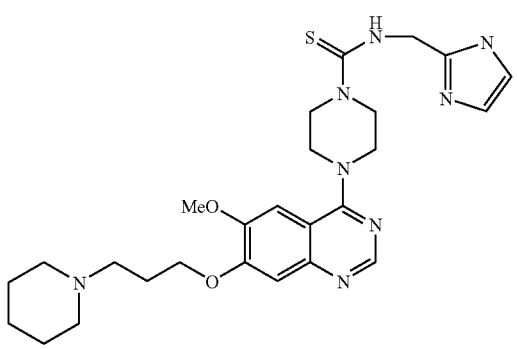

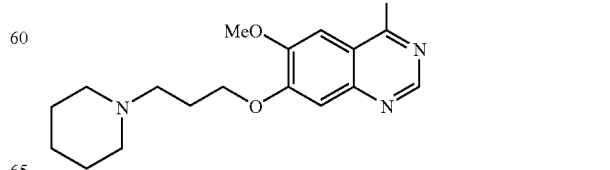

25

{4-[6-methoxy-7-(3-morpholin-4-ylpropoxy)quinazolin-4-yl]piperazinyl}({[6-(trifluoromethyl)(3-pyridyl)]methyl}amino)methane-1-thione

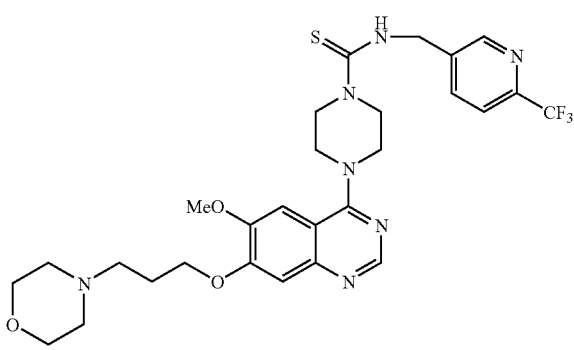

{[(6-chloro(3-pyridyl))methyl]amino}{4-[6-methoxy-7-(2-piperidylethoxy)quinazolin-4-yl]piperazinyl}methane-1-thione

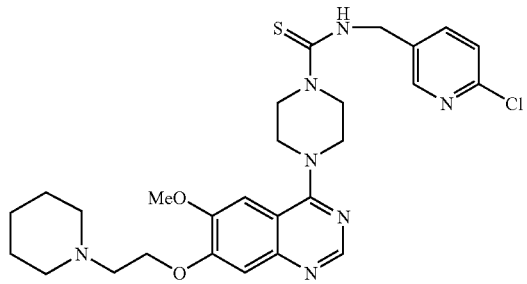

[(benzo[b]furan-3-ylmethyl)amino]{4-[6-methoxy-7-(2-piperidylethoxy)quinazolin4-yl]piperazinyl}methane-1-thione

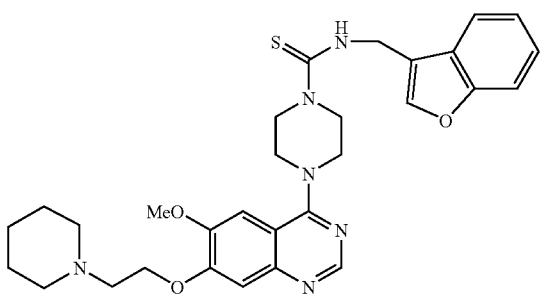

26

{4-[6-methoxy-7-(2-piperidylethoxy)quinazolin-4-yl]piperazinyl}[(2-naphthylmethyl)amin methane-1-thione

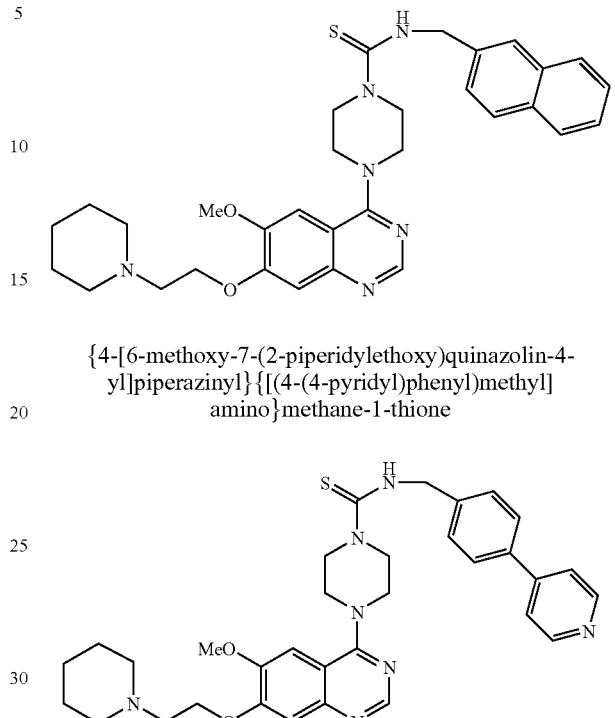

{4-[6-methoxy-7-(2-piperidylethoxy)quinazolin-4-yl]piperazinyl}{[(4-(4-pyridyl)phenyl)methyl]amino}methane-1-thione

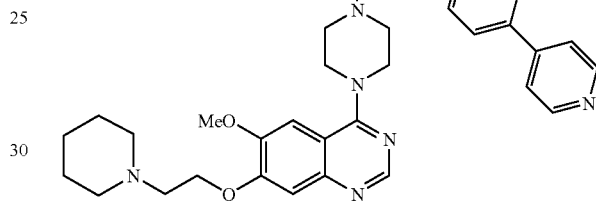

and all pharmaceutically acceptable isomers, salts, hydrates, solvates and prodrug derivatives thereof.

The compounds may be prepared using methods and procedures as generally described in WO 98/14431 published Sep. 12, 1998, which is incorporated herein by reference. Starting materials may be made or obtained as described therein as well. Leaving groups such as halogen, lower alkoxy, lower alkylthio, lower alkylsulfonyloxy, arylsulfonyloxy, etc, may be utilized when necessary except for the reaction point, followed by deprotection. Suitable amino protective groups are, for example, those described in T. W. Greene, Protective Groups in Organic Synthesis, John Wiley & Sons Inc. (1981), etc., such as ethoxycarbonyl, t-butoxycarbonyl, acetyl and benzyl. The protective groups can be introduced and eliminated according to conventional methods used in organic synthetic chemistry [e.g., T. W. Greene, Protective Groups in Organic Synthesis, John Wiley & Sons Inc. (1981)].

In such processes, if the defined groups change under the conditions of the working method or are not appropriate for carrying out the method, the desired compound can be obtained by using the methods for introducing and eliminating protective groups which are conventionally used in organic synthetic chemistry [e.g., T. W. Greene, Protective Groups in Organic Synthesis, John Wiley & Sons Inc. (1981)], etc. Conversion of functional groups contained in the substituents can be carried out by known methods [e.g., R. C. Larock, Comprehensive Organic Transformations (1989)] in addition to the above-described processes, and some of the active compounds of formula I may be utilized as intermediates for further synthesizing novel derivatives according to formula I.

The intermediates and the desired compounds in the processes described above can be isolated and purified by purification methods conventionally used in organic synthetic chemistry, for example, neutralization, filtration, extraction, washing, drying, concentration, recrystallization, and various kinds of chromatography. The intermediates may be subjected to the subsequent reaction without purification.

There may be tautomers for some formula I, and the present invention covers all possible isomers including tautomers and mixtures thereof. Where chiral carbons lend themselves to two different enantiomers, both enantiomers are contemplated as well as procedures for separating the two enantiomers.

In the case where a salt of a compound of formula I is desired and the compound is produced in the form of the desired salt, it can be subjected to purification as such. In the case where a compound of formula I is produced in the free state and its salt is desired, the compound of formula I is dissolved or suspended in a suitable organic solvent, followed by addition of an acid or a base to form a salt.

The following non-limiting reaction Schemes I and II illustrate preferred embodiments of the invention with respect to making compounds according to the invention.

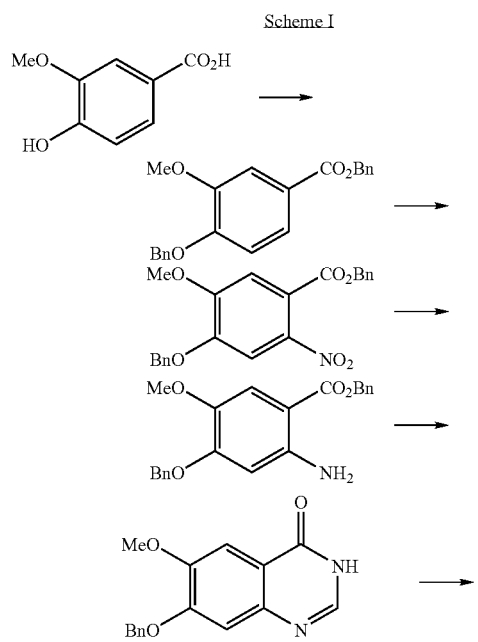

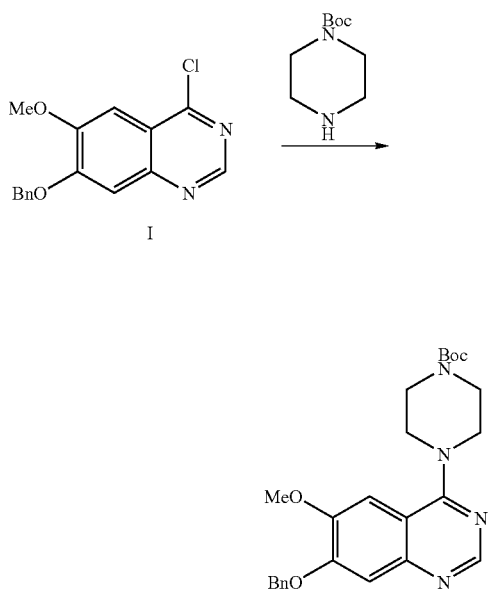

This synthesis of a tert-butyl-4-[6-methoxy-7-(phenyl-methoxy)quinazolin-4-yl]-piperazine carboxylate compound, provides an intermediate that can be utilized in the synthesis of various compounds (the scheme can be adapted to produce bicyclic position isomers) as described above for formula I. The vanilic acid is benzylated, followed by nitration with fuming nitric acid at about 100° C. The nitro functionality is reduced with a reducing agent such as tin chloride, and the like, followed by cyclization with a base such as formamide at elevated temperature, preferably in the range 100 to 200° C. to afford quinazolinone. The synthesis of 4-Cl-quinazoline is effected by treating quinazolinone with halogenating reagents such as thionyl chloride, oxalyl chloride and phosphorous oxychloride in presence of solvent such as toluene, or carbon tetrachloride. This intermediate is obtained by treating 4-Cl-quinazoline with Boc-piperazine in an appropriate solvent, such as isopropanol, acetonitrile, or TIE at room or reflux temperature for 1-6 h in presence of base triethylamine or pyridine.

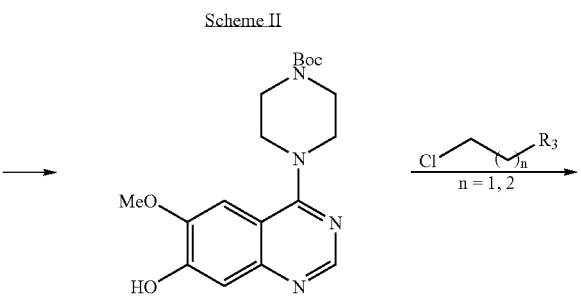

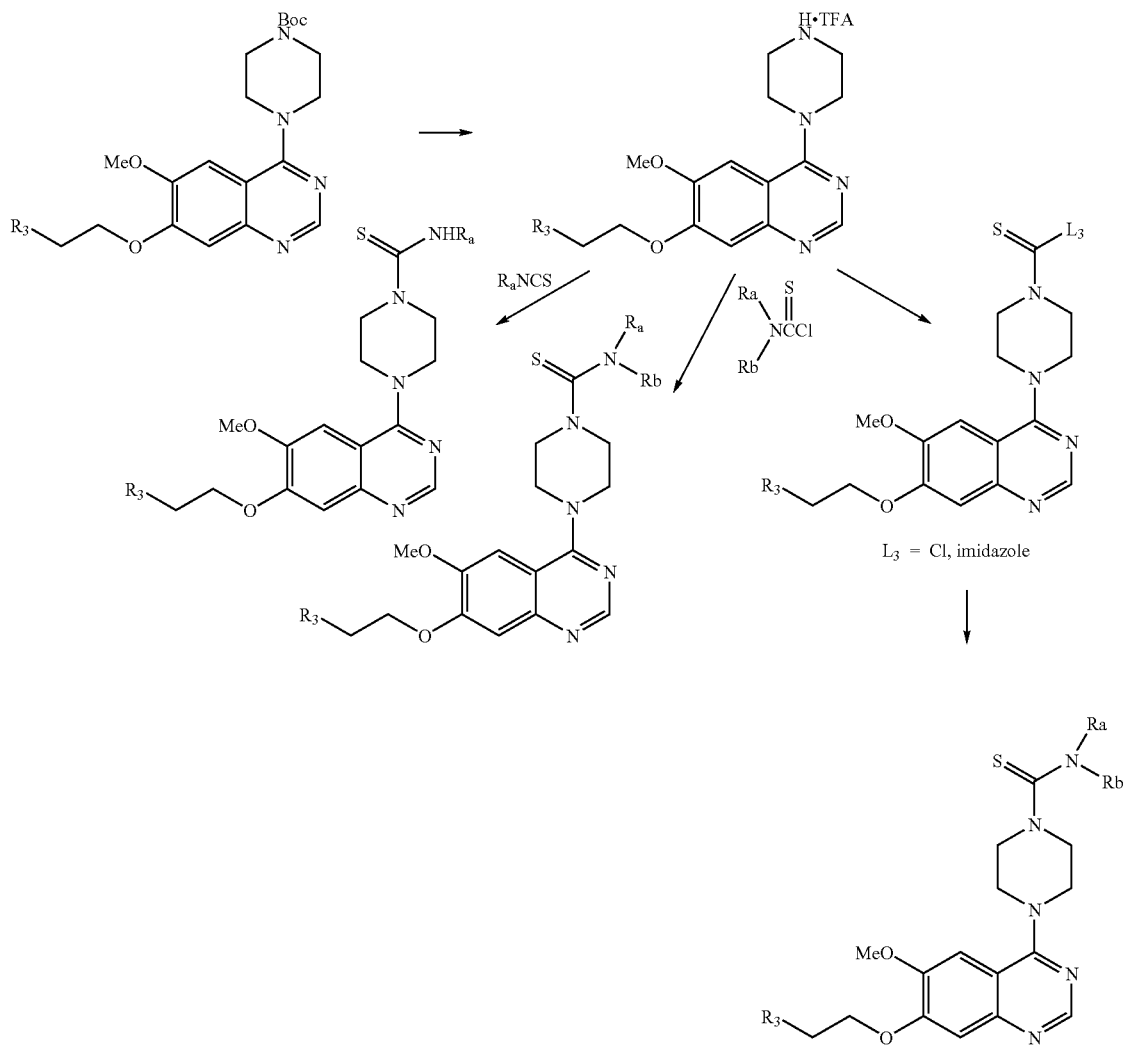

This illustrated Scheme 2 provides the synthesis of various substituted thiourea intermediates from the intermediate obtained in Scheme 1, or by other procedures. The intermediate form Scheme 1 (or its bicyclic position isomer) is debenzylated under hydrogenation conditions followed by alkylation with various substituted alkyl halides. Deprotection of Boc group is effected by trifluoroacetic acid followed by treatment with various isothiocyanates to afford the final thiourea compounds. In cases where the isothiocyanates are not commercially available, the piperazine intermediate may be treated with thiophosgene to give a thiocarbamoyl chloride intermediate followed by reaction with various substituted anilines or benzylamine or heteroarylamines. The piperazine intermediate can also be treated with thiocarbonyldiimidazole to afford a thioacyl imidazole intermediate that can be treated with various anilines or benzylamines or heteroarylamines to afford the desired thioureas. If the thiourea compound has a terminal $NH_2$ group (or one or more of the hydrogen atoms on this amino group is replaced by a displaceable substituent), then this compound may be utilized as an intermediate compound with which to produce a thiourea compound terminated with a —NH—$CH_2$-phenyl-$R^1$ groups. Alternatively, if a different $R^1$ group is desired on the phenyl group, a replaceable para position leaving group phenyl substituent may be displaced after coupling to provide the particular $R^1$ substituent as described for formula I, above.

Such procedures for producing the claimed compounds are merely an illustration of a preferred aspect of the invention. Other procedures and adaptations will be apparent to one of ordinary skill in the art upon views these reaction schemes and the structures of the compounds according to the invention. Such procedures are deemed to be within the scope of the present invention.

Also, the compounds of formula I and pharmaceutically acceptable salts thereof may exist in the form of adducts with water (hydrates) or various solvents, which are also within the scope of the present invention.

The following non-limiting examples are provided to better illustrate the present invention.

EXAMPLE 1

Synthesis of 6-methoxy-7-(2-piperidylethoxy)-4-piperazinylquinazoline intermediate:

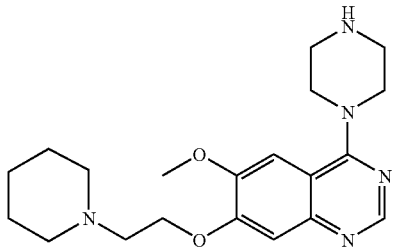

Step A: To the DMF (300 mL) solution of the vanillic acid (25 g, 149 mmol), was added KC2CO3 (102.7 g, 744 mmol, BnBr (44.2 g, 372 mmol), and the resulting suspension was stirred at room temperature overnight. The reaction mixture was filtered, EtOAc was added and the solution was washed with brine, dried, and concentrated. Purification on silica gel chromatography gave 55 g (96%) of the intermediate product. MS(ES) 349 (M+H)+

Step B: To the $CH_2Cl_2$ solution (100 mL) of benzyl protected material from Step A (20 g, 57.4 mmol) at −10° C. was slowly added acetic acid (100 mL). To this cold solution slowly added conc. $HNO_3$ (25.8 mL, 574.4 mmol) and the reaction was warmed to rt. followed by reflux overnight at 100° C. After overnight poured the reaction into ice, extracted the product with EtOAc and washed with brine and dried with MgSO4. The solvent was removed in vacuo to afford the desired intermediate product as a yellow solid (21.8 g, 96.5%). MS(ES) 416 (M+Na).

Step C: To the EtOAc solution (100 mL) of nitro material from Step B (10.9 g, 27.7 mmol) added $SnCl_2.H2O$ (18.7 g, 83.1 mmol) and the reaction mixture was heated at 50° C. overnight. After cooling the reaction mixture was filtered through celite, and the filtrate was washed with 10% $NaHCO_3$, extracted with EtOAc. The organic layers dried, evaporated to afford the intermediate amino product as a brown solid (9.5 g, 95%). MS(ES) 364 (M+H).

Step D: The amino product (3 g, 8.3 mmol) from Step C was dissolved in formamide (20 mL) to this was added ammonium formate (781 mg, 12.4 mmol) and the reaction mixture was heated at 150° C. for 4 h. During this period entire starting material was consumed by HPLC, after cooling poured the reaction into water to afford creamy precipitate. The precipitate was collected by filtration, which is the desired intermediate, cyclized 7-benzyloxy-6-methoxy-4-quinazolinone (1.9 g, 81%). MS(ES) 283(N+H).

Step E: A mixture of 7-benzyloxy-6-methoxy-4-quinazolinone (1 g, 3.5 mmol, from Step D), thionyl chloride (5 mL) and DMF (5 drops) was heated at reflux for 4 h. After cooling excess thionyl chloride was removed by evaporation and the residue azeotroped with toluene to afford the intermediate, 4-chloro-6-methoxy-7-benzyloxyquinazoline, as a yellow solid (652 mg, 62%). MS(ES) 301 (M+H).

Step F: To the THF solution (20 mL) of 4-chloro-6-methoxy-7-benzyloxyquinazoline (1.8 g, 6 mmol) added Boc-piperazine (2.2 g, 12 mmol) followed by DIEA (4.2 mL, 24 mmol) and heated the reaction overnight at 50° C. The solvent was evaporated, the residue dissolved in water and extracted the product with EtOAc. The EtOAc layer was dried, filtered and evaporated to give the intermediate tert-butyl 4-[6-methoxy-7-phenylmethoxy)quinazolin-4-yl]piperazinecarboxylate as a white solid (2.2 g, 81%). MS(ES) 451 (M+H).

Step G: The benzyloxy compound from Step F (500 mg, 1.1 mmol) was dissolved in EtOH (5 mL), to this added $Pd(OH)_2/C$ (50 mg) and the mixture was placed on the Parr hydrogenator at 50 psi $H_2$ pressure for overnight. The reaction mixture was filtered through celite and washed with EtOH, then evaporated the solvent to afford the intermediate debenzylated material (400 mg, 98%). MS(ES) 361 (M+H)

Step H: To the DMF solution (10 mL) of tert-butyl 4-(7-hydroxy-6-methoxyquinazolin-4-yl)piperazinecarboxylate (1.88 g, 5 mmol), $Cs_2CO_3$ (3.3 g, 10 mmol) added 1-chloroethyl-tosylate (1.8 mL, 10 mmol). The mixture was stirred overnight at room temperature. The solvent was evaporated and the crude residue was purified by RP-HPLC to afford the intermediate tert-butyl-4-[6-methoxy-7-(2-chloroethoxy)quinazolin-4-yl]piperazinecarboxylate as the desired product (850 mg, 40%). MS(ES) 423 (M+H)

Step I: To the DMF solution (10 mL) of the starting material (450 mg, 1.2 mmol) from Step H added piperidine (1.2 mL, 12 mmol) and the reaction was heated at 80° C. overnight. The solvent was evaporated and the crude residue was purified by RP-HPLC (reverse phase high performance liquid chromatography) to afford tert-butyl-4-[6-methoxy-7-(2-piperidylethoxy)quinazolin-4-yl]piperazinecarboxylate as the desired product (310 mg, 55%). MS(ES) 472 (M+H).

Step H: To tert-butyl-4-[6-methoxy-7-(2-piperidylethoxy)quinazolin-4-yl]piperazine-carboxylate from Step I, (111 mg, 0.3 mmol) was added 4N HCl/dioxane (1 ml) and the reaction was stirred at room temperature for 1 h. The solvent was evaporated and azetroped with pentane several times to afford deboc material, i.e. material without the Boc protecting group.

Synthesis of [2H-benzo[d]]1,3-dioxolan-5-ylmethyl)amino]{4-[6-methoxy-7-(2-piperidylethoxy)quinazolin-4-yl]piperazinyl}methane-1thione:

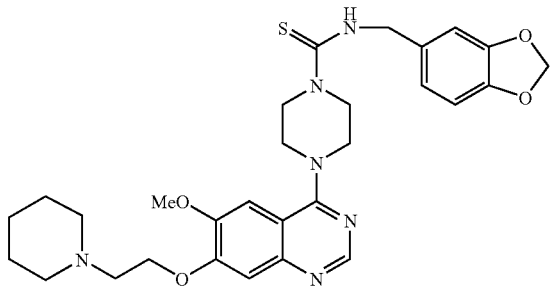

To the $CH_2Cl_2$ solution (40 mL) of thiophosgene (2.51 g, 21.8 mmol) at −10° C. added $CH_2Cl_2$ solution (5 mL) of piperonylamine (3.3 g, 21.8 mmol) dropwise over 10 mins. To this suspension was charged $Et_3N$ (7.6 mL, 52.16 mmol) dropwise over 10 mins, the resulting solution was stirred at 0° C. for 3 h. Then to this solution was added 6-methoxy-7-(2-piperidylethoxy)-4-piperazinylquinazoline (5 g, 18.2 mmol) and the reaction was stirred at 0° C. for 4-5 hr. The insoluble material was filtered off and to the filtrate added EtOAc. The EtOAc layer was washed with water, dried, filtered and evaporated to afford desired product as a tan solid (82%). MS(ES) 565(M+H)

EXAMPLE 2

{4-[6-methoxy-7-(2-piperidylethoxy)quinazolin-4-yl]piperazinyl}{[(5-methylpyrazin-2-yl)methyl]amino}methane-1-thione

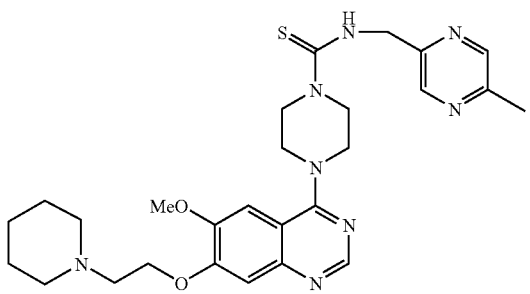

The 6-methoxy-7-(2-piperidylethoxy)-4-piperazinylquinazoline intermediate was synthesized, as described above in Example 1, Step H. To the $CH_2Cl_2$ solution (2 mL) of thiophosgene (0.083 mL, 1.09 mmol) at −10° C. added dropwise $CH_2Cl_2$ solution (4 mL) 6-methoxy-7-(2-piperidylethoxy)-4-piperazinylquinazoline (0.274 g, 1 mmol) and $Et_3N$ (0.348 mL, 2.5 mmol). The reaction mixture was stirred at 0° C. for 1 h, evaporated the solvent and redissolved the residue in DMF (2 mL), to this added DMF solution (2 mL) of 2-aminomethyl-5-methylpyrazine (0.115 mL, 1 mmol). The solution was heated to 70° C. for 3 h, the solvent was evaporated and the residue dissolved in EtOAc. The EtOAc layer was washed with water, dried, filtered and evaporated to afford desired product {4-[6-methoxy-7-(2-piperidylethoxy)quinazolin-4-yl]piperazinyl}{[(5-methylpyrazin-2yl)methyl]amino}methane-1-thione as off-white solid (0.250 g, 60%). MS(ES) 537(M+M)

The pharmacological activities of the compounds of the present invention are obtained by following the test example procedures as follows, for example.

The pharmacological activities of the compounds of the present invention are obtained by following the test example procedures as follows, for example.

Biological Test Assay Type 1

Inhibitory Effect on Compounds on Autophosphorylation of Platelet Derived Growth Factor β-PDGF Receptor (1) HR5 Phosphorylation Assay The HR5 cell line is a cell line of CHO cells engineered to overexpress human β-PDGFR, which cell line is available from the ATCC. The expression level of β-PDGFR in HR5 cells is around $5 \times 10^4$ receptor per cell. For the phosphorylation assay according to the invention, HR5 cells were grown to confluency in 96-well microtiter plates under standard tissue culture conditions, followed by serum-starvation for 16 hours. Quiescent cells were incubated at 37° C. without or with increasing concentrations of the test compound (0.01-30 uM) for 30 minutes followed by the addition of 8 nM PDGF BB for 10 minutes. Cells were lysed in 100 mM Tris, pH 7.5, 750 mM NaCl, 0.5% Triton X-100, 10 mM sodium pyrophosphate, 50 mM NaF, 10 ug/ml aprotinin, 10 ug/nl leupeptin, 1 mM phenylmethylsulfonyl fluoride, 1 mM sodium vanadate, and the lysate was cleared by centrifugation at 15,000×g for 5 minutes. Clarified lysates were transferred into a second microtiter plate in which the wells were previously coated with 500 ng/well of 1B5B11 anti-β-PDGFR mAb, and then incubated for two hours at room temperature. After washing three times with binding buffer (0.3% gelatin, 25 mM Hepes pH 7.5, 100 mM NaCl, 0.01% Tween-20), 250 ng/ml of rabbit polyclonal anti-phosphotyrosine antibody (Transduction Laboratory) was added and plates were incubated at 37° C. for 60 minutes. Subsequently, each well was washed three times with binding buffer and incubated with 1 ug/ml of horse radish peroxidase-conjugated anti-rabbit antibody (Boehringer Mannheim) at 37° C. for 60 minutes. Wells were washed prior to adding ABTS (Sigma), and the rate of substrate formation was monitored at 650 nm. The assay results are reported as $IC_{50}$ (expressed as the concentration of a compound according to the invention that inhibits the PDGF receptor phosphorylation by 50%) as compared to control cells that are not exposed to a compound according to the invention.

Examples of such $IC_{50}$ test results in the HR5 assay for compounds according to the invention are set forth below in Table 1.

(2) MG63 Phosphorylation Assay

The MG63 cell line is a human osteosarcoma tumor cell line available from the ATCC. This assay is for measuring endogenous β-PDGFR phosphorylation in MG63 cells. The assay conditions are the same as those described at for HR5 cell, except that PDGF-BB stimulation is provided in the presence or absence of 45% human plasma. The HR5 assay results are reported as an $IC_{50}$ (expressed as the concentration of a compound according to the invention that inhibits the PDGF receptor phosphorylation by 50%) as compared to control cells that are not exposed to a compound according to the invention.

Examples of such $IC_{50}$ test results in the MG63 assay for compounds according to the invention are set forth below in Table 1.

The assay results for Compound Examples 1 and 2 are set forth in Table 1 below.

TABLE 1

| Example Compound | MG63 w/human plasma $IC_{50}$ (μM) | HR5 $IC_{50}$ (μM) |
| --- | --- | --- |
| Example 1 | 0.129 | 0.05 |
| Example 2 | 0.047 | 0.02 |

Biological Test Assay Type 2

Growth Inhibition Against Smooth Muscle Cells

Vascular smooth muscle cells are isolated from a pig aorta by explanation and used for the test. The cells are put into wells of a 96-well plate (8000 cells/well) and cultured in Dulbeccois modified Eagle's medium (DMEM; Nissui Pharmaceutical Co., Ltd.) containing 10% fetal bovine serum (FBS; Hyclone) for 4 days. Then, the cells are further cultured in DMEM containing 0.1% FBS for 3 days, and are synchronized at the cell growth stationary phase.

To each well is added DMEM containing 0.1% FBS and a test sample at a varied concentration, and the cell growth is brought about by PDGF-BB (SIGMA, final concentration: 20 ng/ml). After culturing for 3 days, the cell growth is measured using a cell growth assay kit (Boehringer Mannheim) according to the XTT method [J. Immunol. Methods, 142, 257-265 (1991)], and the cell growth score is calculated by the following equation.

Cell growth score=$100 \times \{1-(M-PO)/(P100-PO)\}$ wherein P100=absorbance by XTT reagent when stimulated by PDGF-BB; PO=absorbance by XTT reagent when not stimulated by PDGF-BB, and M=absorbance by XTT reagent after addition of a sample when stimulated by PDGF-BB.

The test result is expressed as the concentration of a test compound which inhibits the cell growth by 50% ($IC_{50}$).

Biological Test Assay Type 3

Inhibitory Effect on Hypertrophy of Vascular Intima

Male SD rats (weight: 375-445 g, Charles River, golden standard) are anesthetized with sodium pentobarbital (50 mg/kg, i.p.), and then the neck of each animal is incised by the median incision, followed by retrograde insertion of a balloon catheter (2F, Edwards Laboratories) into the left external carotid. After the above treatment is repeated seven times, the catheter is pulled out, the left external carotid is ligated, and the wound is sutured. A test compound is suspended in a 0.5% solution of Tween 80 in an aqueous solution of sodium chloride to a concentration of 20 mg/ml in the case of intraperitoneal administration and in a 0.5% solution of methyl cellulose 400 to a concentration of 6 mg/ml in the case of oral administration. The suspension is administered once a day in the case of intraperitoneal administration and once or twice a day in the case of oral administration for a period of 15 days starting on the day before the balloon injury. On the 14th day after the balloon injury, the animal is killed and its left carotid is extirpated. The tissues are fixed with formalin, wrapped in paraffin and sliced, followed by Elastica Wangeeson staining. The area of the cross section of the vascular tissues (intima and media) is measured with an image analyzer (Luzex F, NIRECO) and the intima/media area ratio (I/M) is regarded as the degree of hypertrophy of the vascular intima.

From the results obtained, it is apparent when the hypertrophy of vascular intima is significantly inhibited by administration of the compounds of the present invention.

Biological Test Assay Type 4

Evaluation by the Use of a Rat Adjuvant Arthritis Model

Dead cells of Mycobacterium bacterium (Difco Laboratories Inc.) are disrupted in agate mortar and suspended in liquid paraffin to the final concentration of 6.6 mg/ml, followed by sterilization with high pressure steam. Then, 100 ml of the suspension is subcutaneously injected into the right hind foot pad of each animal of groups of female 8-weeks-old Lewis rats (Charles River Japan) (6 animals/group) to induce adjuvant arthritis. A test compound is suspended in a 0.5% solution of methyl cellulose to the final concentration of 3 mg/ml, and from just before the induction of arthritis, the suspension is orally administered in an amount of 100 ml/100 g of the body weight once a day, 5 days a week. To a control group is administered a 0.5% solution of methyl cellulose. A normal group is given no adjuvant treatment or test compound administration. The administration of the test compound is continued till the 18th day after the adjuvant treatment. On the 17th day, the number of leukocytes in peripheral blood are counted, and on the 15th day, all the blood is collected, followed by dissection.

The change in body weight with the passage of time, the change of edema in hind foot with the passage of time, the weight of spleen and thymus, the number of leukocytes in peripheral blood, the hydroxyproline content of urine, the glucosaminoglycan content of urine, the SH concentration in serum, the concentration of nitrogen monoxide in serum and the concentration of mucoprotein in serum are measured and evaluated. The volume of each of both hind feet are measured using a rat's hind foot edema measurement device (TK-101, Unicom). The number of leukocytes in peripheral blood are counted using an automatic multichannel blood cell counter (Sysmex K-2000, To a Iyo Denshi Co., Ltd.). The hydroxyproline content of urine is measured according to the method described in Ikeda, et al., Annual Report of Tokyo Metropolitan Research Laboratories P. H., 36, 277 (1985), and the glucosaminoglycan content is measured according to the method described in Moriyama, et al., Hinyo Kiyo, 40, 565 (1994) and Klompmakers, et al., Analytical Biochemistry, 153, 80 (1986). The SH concentration in serum is measured according to the method described in Miesel, et al., Inflammation, 17, 595 (1993), and the concentration of nitrogen monoxide is measured according to the method of Tracey, et al., Journal of Pharmacology & Experimental Therapeutics, 272, 1011 (1995). The concentration of mucoprotein is measured using Aspro GP Kit (Otsuka Pharmaceutical Co., Ltd.). The percentage inhibition for each indication is calculated according to the following equation.

% Inhibition={(Control group−Compound-administered group)/(Control group−Normal group)}×100.

From the results obtain from such assays, it is apparent when the compound according to the invention inhibits the occurrence of adjuvant arthritis.

Biological Test Assay Type 5

Activity on a Mesangial Proliferative Glomerulonephritis Model

Anti-rat Thy-1.1 monoclonal antibody OX-7 (Sedaren) is administered to male Wister-Kyoto rats (Charles River Japan, 160 g, 6 animals/group) in an amount of 1.0 mg/kg by intravenous administration through the tail vein. A test compound is suspended in a 0.5% solution of methylcellulose and the resulting suspension is administered to each of the rats twice a day for a period of 7 days starting on the day before the administration of OX-7. On the 7th day after the OX-7 administration, when mesangial cell growth and extracellular matrix hypertrophy become prominent, the left kidney of each rat is extirpated, fixed with 20% buffered formalin for 6 hours and wrapped in paraffin, followed by slicing. The obtained pieces are subjected to immune tissue staining using antibody PC10 (DAKO) against an intranuclear antigen of proliferative cells. After comparative staining with Methyl Green staining solution using diaminobenzidine as a color developer, the paraffin pieces are enclosed. Half of the glomeruli in a kidney piece are observed and the number of the cells in one glomerulus which are positive to the intranuclear antigen of proliferative cells are calculated. The test for the significance of difference is carried out by the Wilcoxon test.

From such results, it is apparent when the compounds according to the present invention show alleviating activity on mesangial proliferative glomerulonephritis.

The compounds of formula (I) and pharmaceutically acceptable salts thereof can be administered as such, but it is usually preferred to administer them in the form of pharmaceutical compositions, which are used for animals and human beings.

It is preferred to employ the administration route which is the most effective for the treatment. For example, administration is made orally or non-orally by intrarectal, intraoral, subcutaneous, intramuscular or intravenous administration.

Examples of the forms for administration are capsules, tablets, granules, powders, syrups, emulsions, suppositories and injections.

Liquid compositions such as emulsions and syrups which are appropriate for oral administration can be prepared using water, sugars such as sucrose, sorbitol and fructose, glycols such as polyethylene glycol and propylene glycol, oils such as sesame oil, olive oil and soybean oil, preservatives such as benzoates, flavors such as strawberry flavor and peppermint, etc.

Capsules, tablets, powders and granules can be prepared using excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, plasticizers such as glycerin, etc.

Compositions suitable for non-oral administration preferably comprise a sterilized aqueous preparation containing an active compound which is isotonic to the recipient's blood. For example, injections are prepared using a carrier which comprises a salt solution, a glucose solution, or a mixture of a salt solution and a glucose solution.

Compositions for topical application are prepared by dissolving or suspending an active compound in one or more kinds of solvents such as mineral oil, petroleum and polyhydric alcohol, or other bases used for topical drugs.

Compositions for intestinal administration are prepared using ordinary carriers such as cacao fat, hydrogenated fat and hydrogenated fat carboxylic acid, and are provided as suppositories.

The compositions for non-oral administration may additionally be formulated to contain one or more kinds of additives selected from glycols, oils, flavors, preservatives (including antioxidants), excipients, disintegrating agents, lubricants, binders, surfactants and plasticizers which are used for the preparation of compositions for oral administration.

The effective dose and the administration schedule for each of the compounds of formula (I) or a pharmaceutically acceptable salt thereof will vary depending on the administration route, the patient's age and body weight, and the type or degree of the diseases to be treated. However, it is generally appropriate to administer a compound of formula (I) or a pharmaceutically acceptable salt thereof in a dose of 0.01-1000 mg/adult/day, preferably 5-500 mg/adult/day, in one to several parts.

All the compounds of the present invention can be immediately applied to the treatment of kinase-dependent diseases of mammals as kinase inhibitors, specifically, those relating to tyrosine kinase. Specifically preferred are the compounds which have $IC_{50}$ within the range of 10 nM-10 μM. Even more preferred are compounds which have $IC_{50}$ within the range of 10 μM to −1 μM. Most preferred are compounds which have an $IC_{50}$ value which is smaller than 1 μM.

Specific compounds of the present invention which have an activity to specifically inhibit one of the three types of protein kinase (for example, kinase which phosphorylates tyrosine, kinase which phosphorylates tyrosine and threonine, and kinase which phosphorylates threonine) can be selected. Tyrosine kinase-dependent diseases include hyperproliferative malfunction which is caused or maintained by abnormal tyrosine kinase activity. Examples thereof include psoriasis, pulmonary fibrosis, glomerulonephritis, cancer, atherosclerosis and anti-angiopoiesis (for example, tumor growth and diabetic retinopathy). Current knowledge of the relationship between other classes of kinase and specific diseases is insufficient. However, compounds having specific PTK-inhibiting activity have a useful treatment effect. Other classes of kinase have also been recognized in the same manner. Quercetin, genistein and staurosporin, which are all PTK-inhibitors, inhibit many kinds of protein kinase in addition to tyrosine kinase. However, as a result of their lack of the specificity, their cytotoxicity is high. Therefore, a PTK-inhibitor (or an inhibitor of other classes of kinase) which is apt to bring about undesirable side effects because of the lack of selectivity can be identified by the use of an ordinary test to measure cytotoxicity.

In view of the above description it is believed that one of ordinary skill can practice the invention. The examples given above are non-limiting in that one of ordinary skill in view of the above will readily envision other permutations and variations on the invention without departing from the principal concepts. Such permutations and variations are also within the scope of the present invention.

Although the present invention has been described in some detail by way of illustration for purposes of clarity of understanding, it will be apparent to those of ordinary skill in the art that various modifications and equivalents can be made without departing from the spirit and scope of the invention. It should be understood that the foregoing discussion and examples merely present a detailed description of certain preferred embodiments. All the patents, journal articles and other documents discussed or cited above are herein incorporated by reference in their entirety.

What is claimed is:

1. A compound having formula I(g) or formula I(h) as follows:

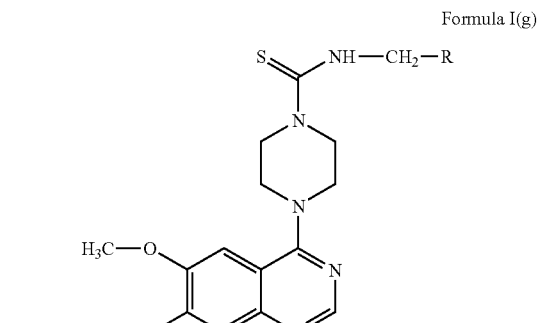

Formula I(g)

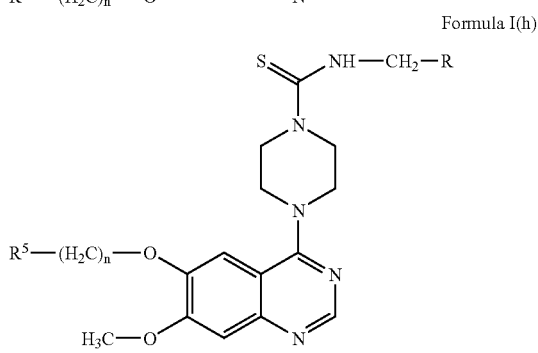

Formula I(h)

wherein

R is a member selected from the group consisting of:
(a) a monocyclic or fused bicyclic heterocyclic ring system having from 5 to 10 ring atoms, wherein 1-4 ring atoms of the ring system are selected from the group consisting of N, O and S, and wherein the ring system may be substituted with 0-2 $R^1$ substituents; and (b)

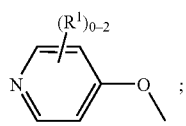

$R^1$ is a member selected from the group consisting of:
halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —NO$_2$, —(CH$_2$)$_m$NR$^2$R$^3$, SO$_2$NR$^2$R$^3$, SO$_2$R$^2$, CF$_3$, OR$^2$, phenyl, naphthyl, and a 5-6 membered aromatic heterocyclic system containing from 1-4 heteroatoms selected from N, O and S, wherein from 1-4 hydrogen atoms on the aromatic heterocyclic system may be independently replaced with a member selected from the group consisting of halo, —C, —$C_4$-alkyl, —CN, —$C_{1-4}$alkyl, —$C_{2-6}$alkenyl, —$C_{2-6}$alkynyl, —$C_{3-8}$cycloalkyl, —$C_{0-4}$alkyl $C_{3-8}$cycloalkyl and —$NO_2$;

$R^2$ and $R^3$ are independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl, $C_{0-4}$alkylnaphthyl, $C_{0-4}$alkylindolyl, and $C_{0-4}$alkylisoquinolyl, wherein from 1-4 hydrogen atoms on the ring atoms of the phenyl, naphthyl, indolyl, or isoquinolyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

m is an integer of 0-2;

n is 2 or 3;

$R^5$ is a member selected from the group consisting of:

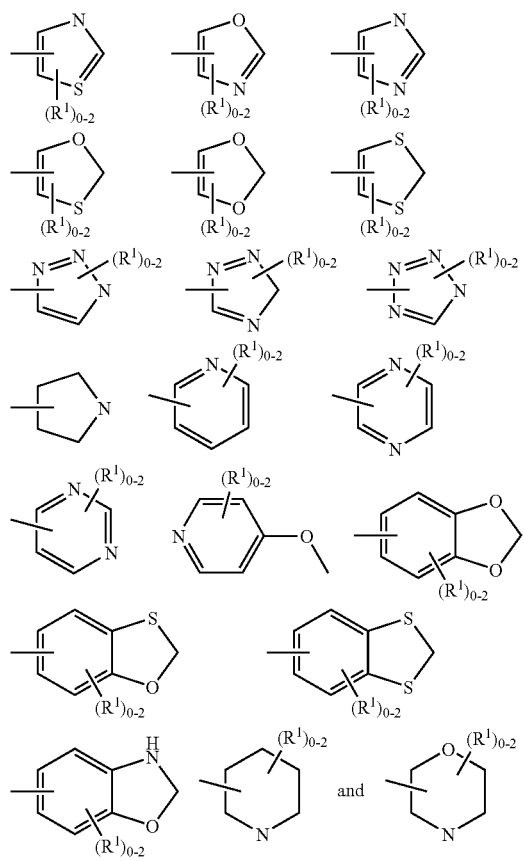

and all pharmaceutically acceptable salts, hydrates, solvates and N-acylated derivatives thereof.

2. The compound according to claim 1, wherein $R^1$ is a member selected from the group consisting of CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy, and all pharmaceutically acceptable salts, hydrates, solvates and N-acylated derivatives thereof.

3. The compound of claim 1, wherein R is a member selected from the group consisting of:

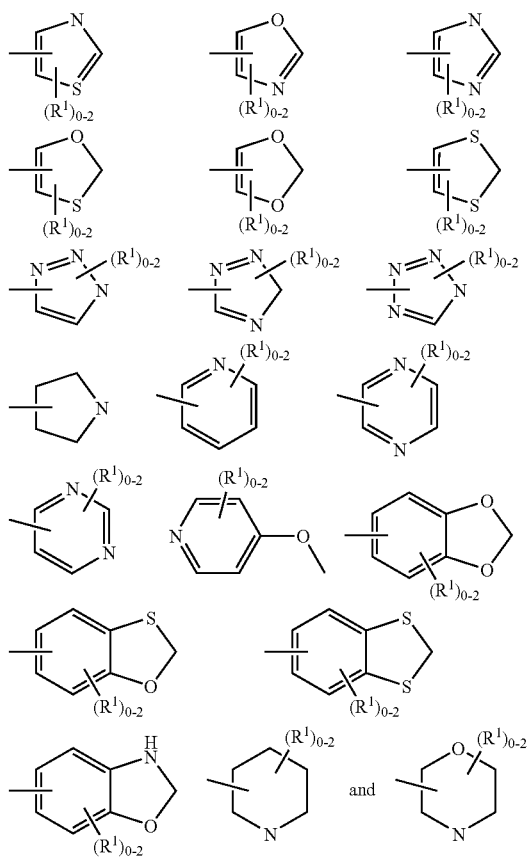

and all pharmaceutically acceptable salts, hydrates, solvates and N-acylated derivatives thereof.

4. The compound of claim 1, wherein R is

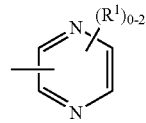

and all pharmaceutically acceptable salts, hydrates, solvates and N-acylated derivatives thereof.

5. The compound of claim 4 wherein R is

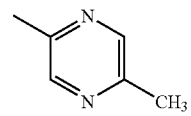

and all pharmaceutically acceptable salts, hydrates, solvates and N-acylated derivatives thereof.

6. The compound of claim 1 of the formula: wherein R is

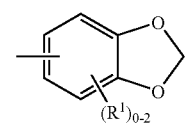

and all pharmaceutically acceptable isomers salts, hydrates, solvates and prodrug derivatives thereof.

7. A compound according to claim 1, selected from the group consisting of:

[(2H-benzo[d]1,3-dioxolan-5-ylmethyl)amino]{4-[6-methoxy-7-(2-piperidylethoxy)quinazolin-4-yl]piperazinyl}methane-1-thione

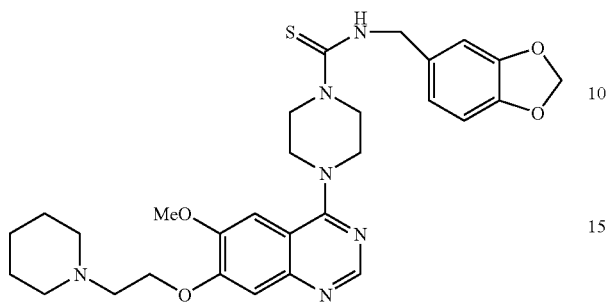

[(2H-benzo[d]1,3-dioxolan-5-ylmethyl)amino]{4-[6-methoxy-7-(2-morpholin-4-ylethoxy)quinazolin-4-yl]piperazinyl}methane-1-thione

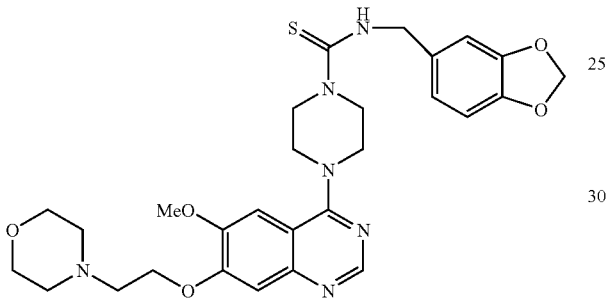

{4-[6-methoxy-7-(2-morpholin-4-ylethoxy)quinazolin-4-yl]piperazinyl}{[(5-methylpyrazin-2-yl)methyl]amino}methane-1-thione

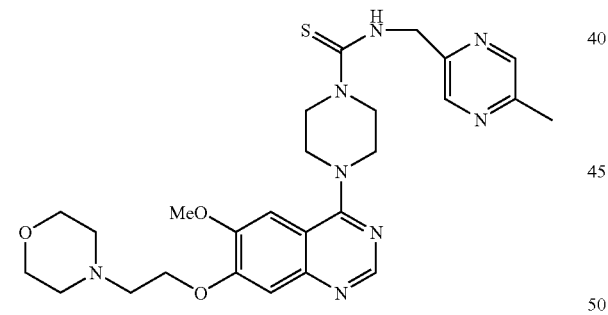

{4-[6-methoxy-7-(2-piperidylethoxy)quinazolin-4-yl]piperazinyl}{[(5-methylpyrazin-2-yl)methyl]amino}methane-1-thione

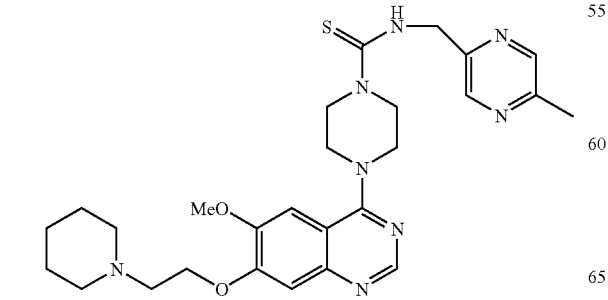

{4-[6-methoxy-7-(2-piperidylethoxy)quinazolin-4-yl]piperazinyl}[(pyrazin-2-ylmethyl)amino]methane-1-thione

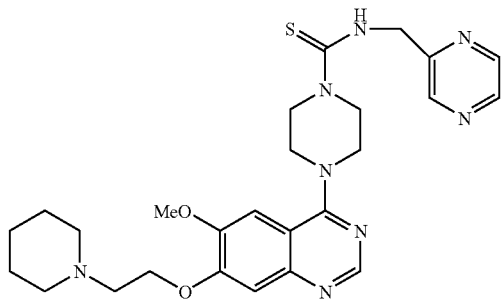

{4-[6-methoxy-7-(2-piperidylethoxy)quinazolin-4-yl]piperazinyl}[(3-pyridylmethyl)amino]methane-1-thione

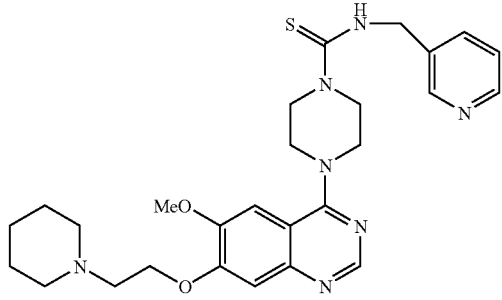

[(2-furylmethyl)amino]{4-[6-methoxy-7-(2-piperidylethoxy)quinazolin-4-yl]piperazinyl}methane-1-thione

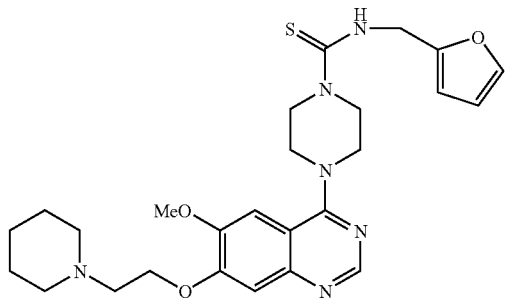

{4-[6-methoxy-7-(2-piperidylethoxy)quinazolin-4-yl]piperazinyl}[(2-thienylmethyl)amino]methane-1-thione

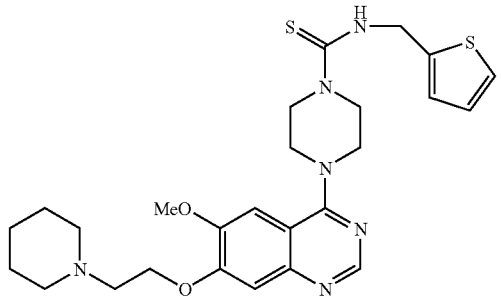

{4-[6-methoxy-7-(2-piperidylethoxy)quinazolin4-yl]piperazinyl}[(1,3-thiazol-2-ylmethyl)amino]methane-1-thione

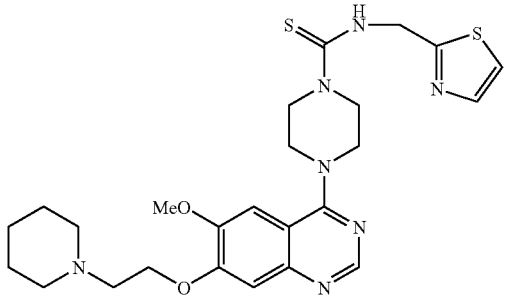

[(imidazol-2-ylmethyl)amino]{4-[6-methoxy-7-(2-piperidylethoxy)quinazolin4-yl]piperazinyl}methane-1-thione

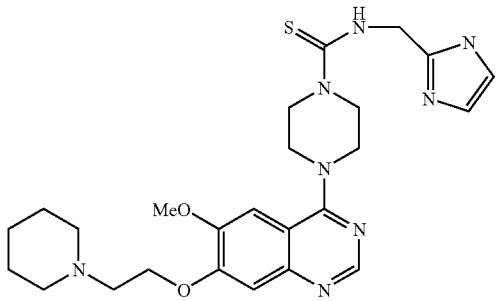

{4-[6-methoxy-7-(3-piperidylpropoxy)quinazolin-4-yl]piperazinyl}{[(5-methylpyrazin-2-yl)methyl]amino}methane-1-thione

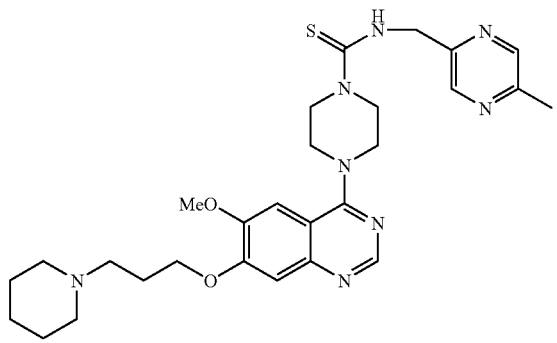

{4-[6-methoxy-7-(3-morpholin-4-ylpropoxy)quinazolin-4-yl]piperazinyl}{[(5-methylpyrazin-2-yl)methyl]amino}methane-1-thione

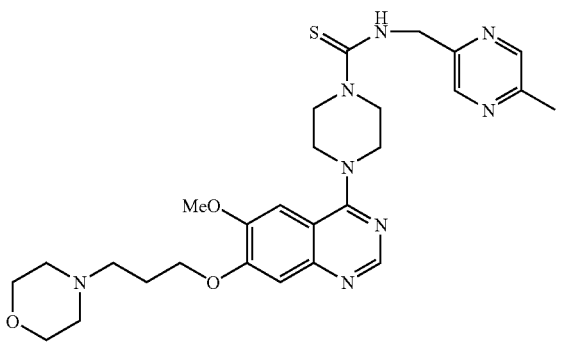

{4-[6-methoxy-7-(3-piperidylpropoxy)quinazolin-4-yl]piperazinyl}[(3-pyridylmethyl)amino]methane-1-thione

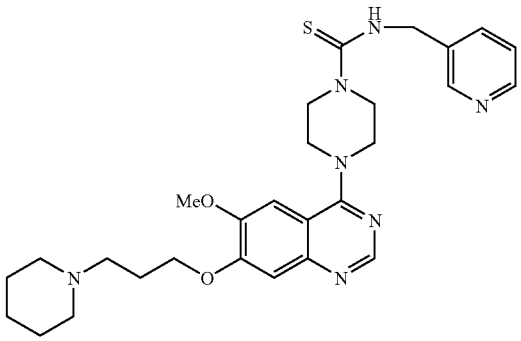

{4-[6-methoxy-7-(3-morpholin-4-ylpropoxy)quinazolin-4-yl]piperazinyl}[(3-pyridylmethyl)amino]methane-1-thione

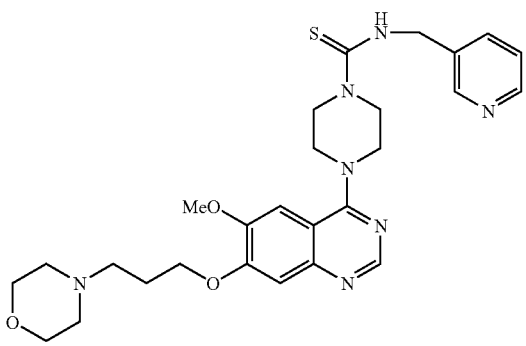

{4-[6-methoxy-7-(3-piperidylpropoxy)quinazolin-4-yl]piperazinyl}[(1,3-thiazol-2-ylmethyl)amino]methane-1-thione

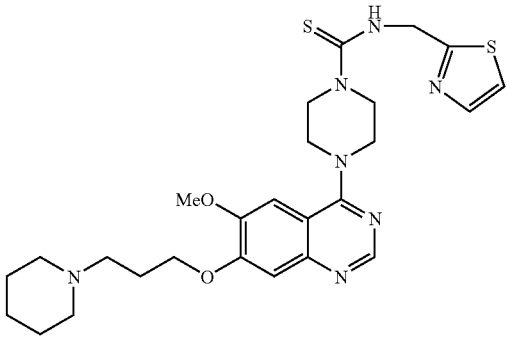

{4-[6-methoxy-7-(3-morpholin-4-ylpropoxy)quinazolin-4-yl]piperazinyl}[(1,3-thiazol-2-ylmethyl)amino]methane-1-thione

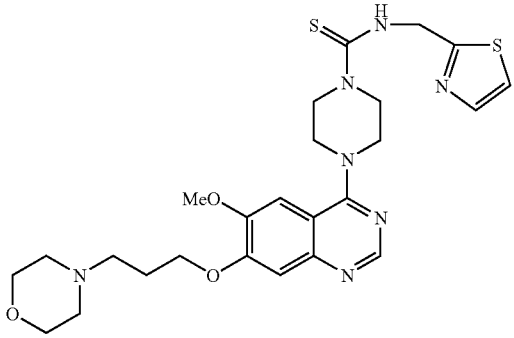

45

[(imidazol-2-ylmethyl)amino]{4-[6-methoxy-7-(3-morpholin-4-ylpropoxy)quinazolin-4-yl]piperazinyl}methane-1-thione

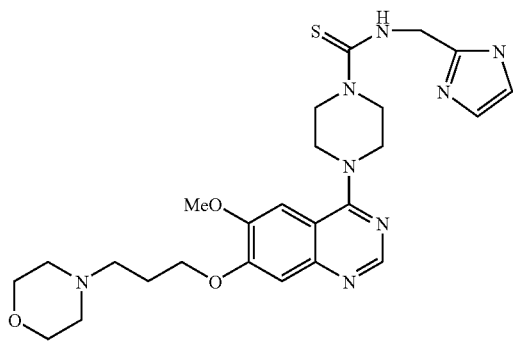

[(imidazol-2-ylmethyl)amino]{4-[6-methoxy-7-(3-piperidylpropoxy)quinazolin-4-yl]piperazinyl}methane-1-thione

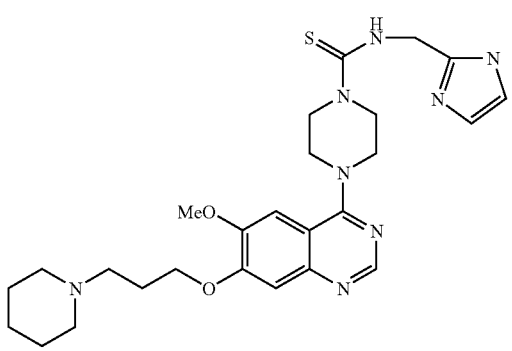

{4-[6-methoxy-7-(3-piperidylpropoxy)quinazolin-4-yl]piperazinyl}{[(6-phenyl(3-pyridyl))methyl]amino}methane-1-thione

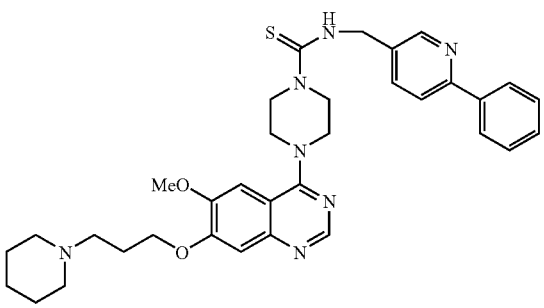

{4-[6-methoxy-7-(3-piperidylpropoxy)quinazolin-4-yl]piperazinyl}{[(6-methyl(3-pyridyl))methyl]amino}methane-1-thione

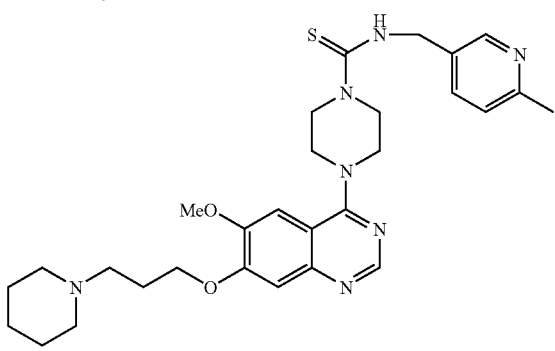

46

{4-[6-methoxy-7-(3-piperidylpropoxy)quinazolin-4-yl]piperazinyl}({[6-(trifluoromethyl)(3-pyridyl)]methyl}amino)methane-1-thione

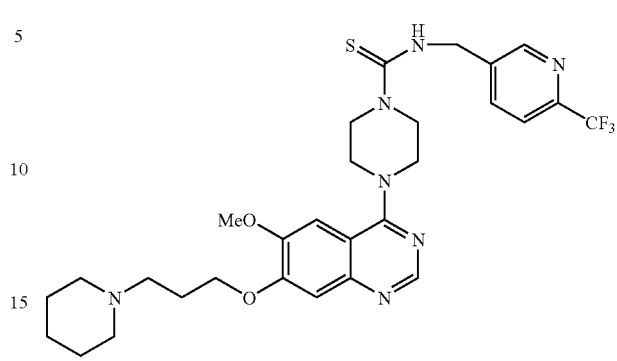

{4-[6-methoxy-7-(3-morpholin-4-ylpropoxy)quinazolin-4-yl]piperazinyl}({[6-(trifluoromethyl)(3-pyridyl)]methyl}amino)methane-1-thione

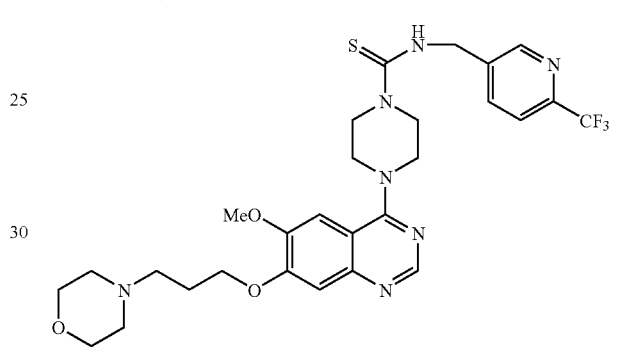

{[(6-chloro(3-pyridyl))methyl]amino}{4-[6-methoxy-7-(2-piperidylethoxy)quinazolin-4-yl]piperazinyl}methane-1-thione

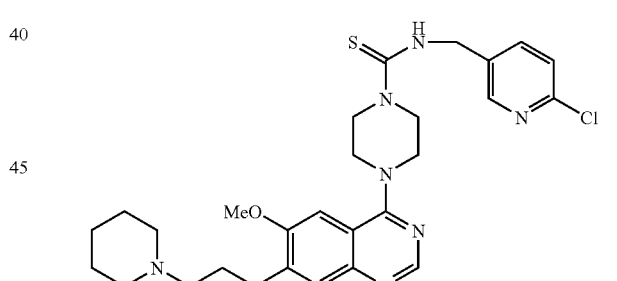

[(benzo[b]furan-3-ylmethyl)amino]{4-[6-methoxy-7-(2-piperidylethoxy)quinazolin-4-yl]piperazinyl}methane-1-thione

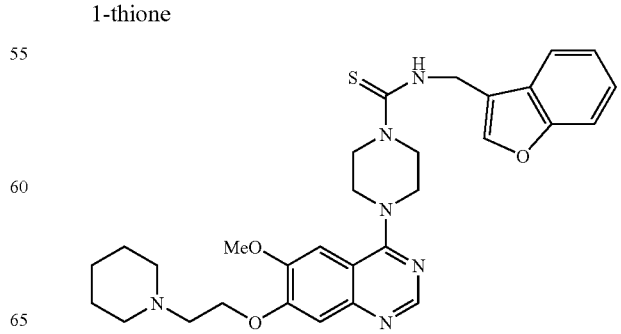

and all pharmaceutically acceptable salts, hydrates, and solvate thereof.

8. A pharmaceutical composition comprising an effective amount of a compound according to claim 1, or a pharmaceutically acceptable salt thereof, and a pharmaceutically acceptable diluent or carrier.

* * * * *

UNITED STATES PATENT AND TRADEMARK OFFICE
CERTIFICATE OF CORRECTION

PATENT NO. : 7,329,655 B2
APPLICATION NO. : 10/344625
DATED : February 12, 2008
INVENTOR(S) : Anjali Pandey et al.

It is certified that error appears in the above-identified patent and that said Letters Patent is hereby corrected as shown below:

In The Claims:

Claim 1, Column 39, Line 6, delete "-C,"
Claim 1, Column 39, Line 7, delete "-$C_4$-alkyl,"

Signed and Sealed this

Twentieth Day of April, 2010

David J. Kappos
*Director of the United States Patent and Trademark Office*